# (12) United States Patent
Vu

(10) Patent No.: US 7,354,927 B2
(45) Date of Patent: Apr. 8, 2008

(54) 6H-[1]BENZOPYRANO[4,3-B]QUINOLINES AND THEIR USE AS ESTROGENIC AGENTS

(75) Inventor: An T. Vu, Pottstown, PA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 11/219,940

(22) Filed: Sep. 6, 2005

(65) Prior Publication Data

US 2006/0052410 A1    Mar. 9, 2006

Related U.S. Application Data

(60) Provisional application No. 60/607,766, filed on Sep. 7, 2004.

(51) Int. Cl.
A61K 31/4741    (2006.01)
C07D 491/052    (2006.01)
(52) U.S. Cl. .......................... 514/285; 546/62; 546/14
(58) Field of Classification Search ................ 514/285; 546/62, 14
See application file for complete search history.

(56) References Cited

U.S. PATENT DOCUMENTS

| | | | |
|---|---|---|---|
| 3,493,579 | A | 2/1970 | Lyle et al. |
| 3,518,258 | A | 6/1970 | von Strandtmann et al. |
| 3,518,272 | A | 6/1970 | von Strandtmann et al. |
| 3,518,273 | A | 6/1970 | von Strandtmann et al. |
| 3,541,100 | A | 11/1970 | Ramirez et al. |
| 3,551,565 | A | 12/1970 | Clarke et al. |
| 3,600,375 | A | 8/1971 | Wang et al. |
| 4,418,068 | A | 11/1983 | Jones |
| 5,318,976 | A | 6/1994 | Luzzio et al. |
| 5,998,402 | A | 12/1999 | Miller et al. |
| 6,110,962 | A | 8/2000 | Wrobel et al. |
| 2002/0140132 | A1 | 10/2002 | Guarr et al. |
| 2002/0183310 | A1 | 12/2002 | Miller et al. |
| 2003/0087955 | A1 | 5/2003 | Miller et al. |
| 2003/0166643 | A1 | 9/2003 | Mcdevitt |
| 2003/0171412 | A1 | 9/2003 | Malamas et al. |
| 2003/0199570 | A1 | 10/2003 | Coghlan et al. |

FOREIGN PATENT DOCUMENTS

| | | |
|---|---|---|
| EP | 376166 | 7/1990 |
| GB | 2361642 | 10/2001 |
| GB | 2374412 | 10/2002 |
| JP | 63295579 A | 1/1988 |
| JP | 63238079 A | 4/1988 |
| SU | 1051092 | 7/1982 |
| WO | 264124 | 10/1986 |
| WO | WO 94/20869 | 9/1994 |
| WO | WO 95/06640 | 3/1995 |
| WO | WO 96/10015 | 4/1996 |
| WO | WO 96/19458 | 6/1996 |
| WO | WO 97/09348 | 3/1997 |
| WO | WO 98/45272 | 10/1998 |
| WO | WO 99/07847 | 2/1999 |
| WO | WO 89/02739 | 4/1999 |
| WO | WO 00/01716 | 1/2000 |
| WO | WO 00/59897 | 10/2000 |
| WO | WO 00/61230 | 10/2000 |
| WO | WO 00/62765 | 10/2000 |
| WO | WO 00/76529 | 12/2000 |
| WO | WO 01/24785 | 4/2001 |
| WO | WO 01/64665 | 9/2001 |
| WO | WO 01/72713 | 10/2001 |
| WO | WO 02/30407 | 4/2002 |
| WO | WO 02/46164 | 6/2002 |
| WO | WO 02/46168 | 6/2002 |
| WO | WO 02/051821 | 7/2002 |
| WO | WO 02/068548 | 9/2002 |
| WO | WO 03/044006 | 5/2003 |
| WO | WO 03/045930 | 6/2003 |
| WO | WO 03/050095 | 6/2003 |

(Continued)

OTHER PUBLICATIONS

Malecki, N. et al.: Synthesis of condensed quinolines and quinazolines as DNA ligands. Bioorg. & Medicnal Chem. vol. 12, pp. 641-647, Feb. 1, 2004.*
Wright, G. et al.: A study of the catalytic reductive products of 2,3-dihydro-6-methoxy-3-(6-nitroveratrylidene)-4H-benzopyran-4-one. J. Heterocyc. Chem. vol. 13, pp. 1181-1185, 1976.*
Al-Azzawi, "The menopause and its treatment in perspective," *Postgraduate Medical Journal* (2001) 77:292-304.
Bhat et al., "A novel human estrogen receptor beta: identification and functional analysis of additional N-terminal amino acids," *Journal of Steroid Biochemistry & Molecular Biology* (1998) 67(3):233-240.
Black et al., "Uterine bioassay of tamoxifen, trioxifene and a new estrogen antagonist (LY117018) in rats and mice ," *Life Sciences* (1980) 26(17):1453-1458.

(Continued)

Primary Examiner—Charanjit S. Aulakh
(74) Attorney, Agent, or Firm—Arnold S. Milowsky; Michael A. Patané; Pepper Hamilton LLP

(57) ABSTRACT

This invention provides 6H-[1]benzopyrano[4,3-b]quinoline compounds having the formula I:

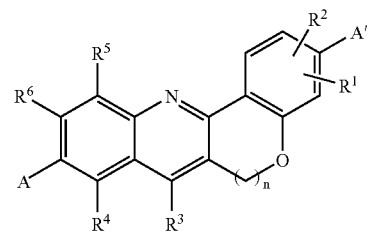

The invention further provides compositions including the compounds, methods for the use of the compounds, and methods of preparation of the compounds.

40 Claims, No Drawings

FOREIGN PATENT DOCUMENTS

| | | |
|---|---|---|
| WO | WO 03/051863 | 6/2003 |
| WO | WO 03/061701 | 7/2003 |
| WO | WO 04/000817 | 12/2003 |
| WO | WO 2004/073610 | 9/2004 |
| WO | WO 2004/094400 | 11/2004 |
| WO | WO 2004/094401 | 11/2004 |
| WO | WO 2004/094451 | 11/2004 |
| WO | WO 2004/099122 | 11/2004 |
| WO | WO 2004/103973 | 12/2004 |
| WO | WO 2005/018636 | 3/2005 |
| WO | WO 2005/051972 | 6/2005 |
| WO | WO 2005/082880 | 9/2005 |
| WO | WO 2005/123757 | 12/2005 |

OTHER PUBLICATIONS

Brincat, "Hormone replacement therapy and the skin," *Maturitas* (2000) 35(2):107-117.

Calvin, "Oestrogens and wound healing," *Maturitas* (2000) 34(3):195-210.

Couse et al., "Tissue distribution and quantitative analysis of estrogen receptor-alpha (ERalpha) and estrogen receptor-beta (ERbeta) messenger ribonucleic acid in the wild-type and ERalpha-knockout mouse," *Endocrinology* (1997) 138(11):4613-4621.

Cowley et al., "Estrogen receptors alpha and beta form heterodimers on DNA," *Journal of Biological Chemistry* (1997) 272(32):19858-19862.

Crandall, "Estrogen replacement therapy and colon cancer: a clinical review," *Journal of Women's Health & Gender-Based Medicine* (1999) 8(9):1155-1166.

Edsall et al., "ERbeta ligands. Part 1: the discovery of ERbeta selective ligands which embrace the 4-hydroxy-biphenyl template," *Bioorganic & Medicinal Chemistry* (2003) 11(16):3457-3474.

Epperson et al., "Gonadal steroids in the treatment of mood disorders," *Psychosomatic Medicine* (1999) 61(5):676-697.

Finking et al., "[The effects of estrogen in the cardiovascular system]," *Zeitschrift fur Kardiologie* (2000) 89(5):442-453.

Fitzpatrick et al., "Expression of estrogen receptor-beta protein in rodent ovary," *Endocrinology* (1999) 140(6):2581-2591.

Goldstein et al., "A pharmacological review of selective oestrogen receptor modulators," *Human Reproduction Update* (2000) 6(3):212-224.

Green et al., "Human oestrogen receptor cDNA: sequence, expression and homology to v-erb-A," *Nature* (1986) 320(6058):134-139.

Hall et al., "The multifaceted mechanisms of estradiol and estrogen receptor signaling," *Journal of Biological Chemistry* (2001) 276(40):36869-36872.

Henke et al., "A new series of estrogen receptor modulators that display selectivity for estrogen receptor beta," *Journal of Medicinal Chemistry* (2002) 45(25):5492-5505.

Hurn et al., "Estrogen as a neuroprotectant in stroke," *Journal of Cerebral Blood Flow & Metabolism* (2000) 20(4):631-652.

Kuiper et al., "Cloning of a novel receptor expressed in rat prostate and ovary," *Proceedings of the National Academy of Sciences of the USA* (1996) 93(12):5925-5930.

Kuiper et al., "Comparison of the ligand binding specificity and transcript tissue distribution of estrogen receptors alpha and beta," *Endocrinology* (1997) 138(3):863-870.

Levin, "Cell localization, physiology, and nongenomic actions of estrogen receptors," *Journal of Applied Physiology* (2001) 91(4):1860-1867.

Levin, "Cellular Functions of the Plasma Membrane Estrogen Receptor," *Trends in Endocrinology & Metabolism* (1999) 10(9):374-377.

McDonnell et al., "The mechanism of action of steroid hormone receptors," Ch. 20, pp. 351-361, *Principles of Molecular Regulation*, Eds. Michael & Means. Totowa, NJ: Humana Press, 2000.

McDonnell, "Selective estrogen receptor modulators (SERMs): A first step in the development of perfect hormone replacement therapy regimen," *Journal of the Society of Gynecologic Investriction* (2000) 7(1 Suppl):S10-S15.

McKenna et al., "Nuclear receptor coregulators: cellular and molecular biology," *Endocrine Review* (1999) 20(3):321-344.

Mendelsohn et al., "The protective effects of estrogen on the cardiovascular system," *New England Journal of Medicine* (1999) 340(23):1801-1811.

Meyers et al., "Estrogen receptor subtype-selective ligands: asymmetric synthesis and biological evaluation of cis- and trans-5,11-dialkyl-5,6,11, 12-tetrahydrochrysenes," *J. Med. Chem.* (1999) 42(13):2456-2468.

Miller et al., "Constrained phytoestrogens and analogues as ERbeta selective ligands," *Bioorganic & Medicinal Chemistry Letters* (2003) 13(14):2399-2403.

Monyer et al., "Glucose deprivation neuronal injury in cortical culture," *Brain Research* (1989) 483(2):347-354.

Moggs et al., "Estrogen receptors: orchestrators of pleiotropic cellular responses," *EMBO Reports* (2001) 2(9):775-781.

Monk et al., "Use of estrogens for the prevention and treatment of Alzheimer's disease," *Dementia & Geriatric Cognitive Disorders* (2000) 11(1):1-10.

Paige et al., "Estrogen receptor (ER) modulators each induce distinct conformational changes in ER alpha and ER beta," *Proceedings of the National Academy of Sciences of the USA* (1999) 96(7):3999-4004.

Pelzer et al., "Estrogen effects in the myocardium: inhibition of NF-kappaB DNA binding by estrogen receptor-alpha and -beta," *Biochemical & Biophysical Research Communications* (2001) 286(5):1153-1157.

Peele et al., "Effects of selection delays on radial maze performance: acquisition and effects of scopolamine," *Pharmacology, Biochemistry and Behavior* (1988) 29(1):143-150.

Pike et al., "Structure of the ligand-binding domain of oestrogen receptor beta in the presence of a partial agonist and a full antagonist," *EMBO J.* (1999) 18(17):4608-4618.

Quaedackers et al., "4-hydroxytamoxifen trans-represses nuclear factor-kappa B activity in human osteoblastic U2-OS cells through estrogen receptor (ER)alpha, and not through ER beta," *Endocrinology* (2001) 142(3):1156-1166.

Sar et al., "Differential expression of estrogen receptor-beta and estrogen receptor-alpha in the rat ovary," *Endocrinology* (1999) 140(2):963-971.

Shiau et al., "The structural basis of estrogen receptor/coactivator recognition and the antagonism of this interaction by tamoxifen," *Cell* (1998) 95(7):927-937.

Wroblewski et al., "Lactic dehydrogenase activity in blood," *Proc. Soc. Exp. Biol. Med.* (1955) 90(1):210-213.

Yagi et al., "A simple fluorometric assay for lipoperoxide in blood plasma," *Biochem Med.* (1976) 15(2):212-216.

Yang et al, "Synthesis and structure-activity relationship of 3-arylbenzoxazines as selective estrogen receptor beta agonists," Bioorganic & Medicinal Chemistry Letters (2004), 14(9), 2327-2330.

Schopfer et al, "Synthesis and characterization of aryl benzthiophenes," *Journal of Medicinal Chemistry* 2002, 45, 1399-1401.

Yang et al, "ERb Ligands. Part 2: Synthesis and structure-activity relationships of a series of 4-hydroxy-biphenyl-carbaldehyde oxime derivatives," Bioorganic & Medicinal Chemistry (2004), 12(10), 2553-2570.

Malamas et al, "Design and Synthesis of Aryl Diphenolic Azoles as Potent and Selective Estrogen Receptor-b Ligands," Journal of Medicinal Chemistry (2004), 47(21), 5021-5040.

Compton et al, "Pyrazolo[1,5-a]pyrimidines: estrogen receptor ligands possessing estrogen receptor b antagonist activity," Journal of Medicinal Chemistry (2004), 47(24), 5872-5893.

De Angelis et al, "Indazole Estrogens: Highly Selective Ligands for the Estrogen Receptor b," Journal of Medicinal Chemistry (2005), 48(4), 1132-1144.

Mewshaw et al, "ERb Ligands. 3. Exploiting Two Binding Orientations of the 2-Phenylnaphthalene Scaffold To Achieve ERb Selectivity," Journal of Medicinal Chemistry (2005), 48(12), 3953-3979.

McDevitt et al, "Estrogen receptor ligands: design and synthesis of new 2-arylindene-1-ones," Bioorganic & Medicinal Chemistry Letters (2005), 15(12), 3137-3142.

Vu et al, "ERb ligands. Part 4: Synthesis and structure-activity relationships of a series 2-phenylquinoline derivatives," Bioorganic & Medicinal Chemistry Letters (2005), 15(20), 4520-4525.

De Angelis et al, "Isocoumarins as estrogen receptor beta selective ligands: Isomers of isoflavone phytoestrogens and their metabolites," Bioorganic & Medicinal Chemistry (2005), 13(23), 6529-6542.

Chesworth et al, "Estrogen receptor b selective ligands: Discovery and SAR of novel heterocyclic ligands," Bioorganic & Medicinal Chemistry Letters (2005), 15(24), 5562-5566.

Collini et al, "7-Substituted 2-phenyl-benzofurans as ERb selective ligands," Bioorganic & Medicinal Chemistry Letters (2004), 14(19), 4925-4929.

Malecki et al., "Synthesis of condensed quinolines and quinazolines as DNA ligands," *Bioorganic & Medicinal Chemistry* (2004) 12(3):641-647.

* cited by examiner

6H-[1]BENZOPYRANO[4,3-B]QUINOLINES AND THEIR USE AS ESTROGENIC AGENTS

CROSS REFERENCE TO RELATED APPLICATION

This application claims priority benefit of U.S. Provisional Application Ser. No. 60/607,766 filed Sep. 7, 2005, which is incorporated herein by reference in its entirety.

FIELD OF THE INVENTION

This invention relates to 6H-[1]benzopyrano[4,3-b]quinoline compounds, their use as estrogenic agents, and methods of their preparation.

BACKGROUND OF THE INVENTION

The pleiotropic effects of estrogens in mammalian tissues have been well documented, and it is now appreciated that estrogens affect many organ systems (see Mendelsohn and Karas, *New England Journal of Medicine* 340: 1801-1811 (1999), Epperson, et al., *Psychosomatic Medicine* 61: 676-697 (1999), Crandall, *Journal of Womens Health & Gender Based Medicine* 8: 1155-1166 (1999), Monk and Brodaty, *Dementia & Geriatric Cognitive Disorders* 11: 1-10 (2000), Hurn and Macrae, *Journal of Cerebral Blood Flow & Metabolism* 20: 631-652 (2000), Calvin, *Maturitas* 34: 195-210 (2000), Finking, et al., *Zeitschrift fur Kardiologie* 89: 442-453 (2000), Brincat, *Maturitas* 35: 107-117 (2000), Al-Azzawi, *Postgraduate Medical Journal* 77: 292-304 (2001)). Estrogens can exert effects on tissues in several ways, and the most well characterized mechanism of action is their interaction with estrogen receptors leading to alterations in gene transcription. Estrogen receptors are ligand-activated transcription factors and belong to the nuclear hormone receptor superfamily. Other members of this family include the progesterone, androgen, glucocorticoid and mineralocorticoid receptors. Upon binding ligand, these receptors dimerize and can activate gene transcription either by directly binding to specific sequences on DNA (known as response elements) or by interacting with other transcription factors (such as AP1), which in turn bind directly to specific DNA sequences (see Moggs and Orphanides, *EMBO Reports* 2: 775-781 (2001), Hall, et al., *Journal of Biological Chemistry* 276: 36869-36872 (2001), McDonnell, *Principles of Molecular Regulation* 351-361 (2000)). A class of "coregulatory" proteins can also interact with the ligand-bound receptor and further modulate its transcriptional activity (see McKenna, et al., *Endocrine Reviews* 20: 321-344 (1999)). It has also been shown that estrogen receptors can suppress NFκB-mediated transcription in both a ligand-dependent and independent manner (see Quaedackers, et al., *Endocrinology* 142: 1156-1166 (2001), Bhat, et al., *Journal of Steroid Biochemistry & Molecular Biology* 67: 233-240 (1998), Peizer, et al., *Biochemical & Biophysical Research Communications* 286: 1153-7 (2001)).

Estrogen receptors can also be activated by phosphorylation. This phosphorylation is mediated by growth factors such as EGF and causes changes in gene transcription in the absence of ligand (see Moggs and Orphanides, *EMBO Reports* 2: 775-781 (2001), Hall, et al., *Journal of Biological Chemistry* 276: 36869-36872 (2001)).

A less well-characterized means by which estrogens can affect cells is through a so-called membrane receptor. The existence of such a receptor is controversial, but it has been well documented that estrogens can elicit very rapid non-genomic responses from cells. The molecular entity responsible for transducing these effects has not been definitively isolated, but there is evidence to suggest it is at least related to the nuclear forms of the estrogen receptors (see Levin, *Journal of Applied Physiology* 91: 1860-1867 (2001), Levin, *Trends in Endocrinology & Metabolism* 10: 374-377 (1999)).

Two estrogen receptors have been discovered to date. The first estrogen receptor was cloned about 15 years ago and is now referred to as ERα (see Green, et al., *Nature* 320: 134-9 (1986)). The second form of the estrogen receptor was found comparatively recently and is called ERβ (see Kuiper, et al., *Proceedings of the National Academy of Sciences of the United States of America* 93: 5925-5930 (1996)). Early work on ERβ focused on defining its affinity for a variety of ligands and indeed, some differences with ERα were seen. The tissue distribution of ERβ has been well mapped in the rodent and it is not coincident with ERα. Tissues such as the mouse and rat uterus express predominantly ERα, whereas other tissues such as the mouse and rat lung express predominantly ERβ (see Couse, et al., *Endocrinology* 138: 4613-4621 (1997), Kuiper, et al., *Endocrinology* 138: 863-870 (1997)). Even within the same organ, the distribution of ERα and ERβ can be compartmentalized. For example, in the mouse ovary, ERβ is highly expressed in the granulosa cells and ERα is restricted to the thecal and stromal cells (see Sar and Welsch, *Endocrinology* 140: 963-971 (1999), Fitzpatrick, et al., *Endocrinology* 140: 2581-2591 (1999)). However, there are examples where the receptors are coexpressed and there is evidence from in vitro studies that ERα and ERβ can form heterodimers (see Cowley, et al., *Journal of Biological Chemistry* 272: 19858-19862 (1997)).

A large number of compounds have been described that either mimic or block the activity of 17β-estradiol. Compounds having roughly the same biological effects as 17β-estradiol, the most potent endogenous estrogen, are referred to as "estrogen receptor agonists". Those which, when given in combination with 17β-estradiol, block its effects are called "estrogen receptor antagonists". In reality there is a continuum between estrogen receptor agonist and estrogen receptor antagonist activity, and indeed, some compounds behave as estrogen receptor agonists in some tissues and estrogen receptor antagonists in others. These compounds with mixed activity are called selective estrogen receptor modulators (SERMS) and are therapeutically useful agents (e.g., EVISTA®) (see McDonnell, *Journal of the Society for Gynecologic Investigation* 7: S10-S15 (2000), Goldstein, et al., *Human Reproduction Update* 6: 212-224 (2000)). The precise reason why the same compound can have cell-specific effects has not been elucidated, but the differences in receptor conformation and/or in the milieu of coregulatory proteins have been suggested.

It has been known for some time that estrogen receptors adopt different conformations when binding ligands. However, the consequence and subtlety of these changes have been only recently revealed. The three dimensional structures of ERα and ERβ have been solved by co-crystallization with various ligands and clearly show the repositioning of helix 12 in the presence of an estrogen receptor antagonist, which sterically hinders the protein sequences required for receptor-coregulatory protein interaction (see Pike, et al., *Embo* 18: 4608-4618 (1999), Shiau, et al., *Cell* 95: 927-937 (1998)). In addition, the technique of phage display has been used to identify peptides that interact with estrogen receptors in the presence of different ligands (see Paige, et al., *Proceedings of the National Academy of Sciences of the United States of America* 96: 3999-4004 (1999)). For example, a peptide was identified that distinguished between ERα bound to the full estrogen receptor agonists 17β-estradiol and diethylstilbesterol. A different peptide was shown to distinguish between clomiphene bound to ERα and ERβ. These data indicate that each ligand potentially places the receptor in a unique and unpredictable conformation that is likely to have distinct biological activities.

As mentioned above, estrogens affect a panoply of biological processes. In addition, where gender differences have been described (e.g. disease frequencies, responses to challenge, etc.), it is possible that the explanation involves the difference in estrogen levels between males and females. Given the importance of these compounds, it can be seen that there is a need for new estrogenic agents. This invention is directed to these, as well as other, important ends.

SUMMARY OF THE INVENTION

The present invention provides 6H-[1]benzopyrano[4,3-b]quinoline compounds that find use as estrogenic agents. In certain embodiments, the compounds have the formula I:

wherein:

A and A' are each independently OH, H or OR;

each R is independently selected from the group consisting of $C_1$-$C_6$ alkyl, alkenyl, benzyl, acyl, aroyl, —C(=O)—OR', sulfonyl and phosphoryl, wherein each R' is independently selected from $C_1$-$C_6$ alkyl, $C_2$-$C_7$ alkenyl, $C_2$-$C_7$ alkynyl, or $C_3$-$C_{10}$ cycloalkyl, each of which are optionally substituted by 1 to 3 substituents selected from $C_1$-$C_6$ alkyl or halogen;

$R^1$ and $R^2$ are independently selected from the group consisting of H, halogen, $C_1$-$C_6$ alkyl, $C_1$-$C_6$ perhaloalkyl, $CF_3$, $C_2$-$C_7$ alkenyl and $C_1$-$C_6$ alkoxy;

$R^3$, $R^4$, $R^5$ and $R^6$ are each independently selected from the group consisting of H, halogen, $CF_3$, $C_1$-$C_6$ perhaloalkyl, $C_1$-$C_6$ alkyl, $C_2$-$C_7$ alkenyl, $C_2$-$C_7$ alkyny, $C_3$-$C_7$ cycloalkyl, $C_1$-$C_6$ alkoxy, CN, —CHO, acyl, phenyl, aryl and heteroaryl;

wherein the alkyl or alkenyl moieties of $R^3$, $R^4$, $R^5$ and $R^6$ can each be optionally substituted with up to three substituents independently selected from halogen, OH, CN, trifluoroalkyl, trifluoroalkoxy, $NO_2$ or phenyl, wherein said phenyl is optionally substituted with up to three independently selected $R^{10}$ groups;

wherein the alkynyl moiety of $R^3$, $R^4$, $R^5$ and $R^6$ can each be optionally substituted with up to three substituents selected from halogen, —CN, —CHO, acyl, trifluoroalkyl, trialkylsilyl or phenyl, wherein said phenyl is optionally substituted with up to three independently selected $R^{10}$ groups;

wherein the phenyl, aryl or heteroaryl moiety of $R^3$, $R^4$, $R^5$ and $R^6$ can each be optionally substituted with up to three substituents selected from halogen, —CN, alkyl, alkoxy, perfluoroalkyl or perfluoroalkoxy;

each $R^{10}$ is independently selected from the group consisting of halogen, $C_1$-$C_6$ alkyl, $C_2$-$C_7$ alkenyl, —OH, $C_1$-$C_6$ alkoxy, —CN, —CHO, —$NO_2$, amino, $C_1$-$C_6$ alkylamino, di-($C_1$-$C_6$)alkylamino, thiol, and $C_1$-$C_6$ alkylthio; and n is 0, 1, 2, or 3; provided that:

at least one of A and A' is not H;

if n is 0, then $R_3$ is not halogen; and at least one of $R^3$, $R^4$ and $R^5$ is halogen, $C_1$-$C_6$ alkyl, $C_2$-$C_7$ alkenyl, $C_2$-$C_7$ alkynyl, $C_3$-$C_7$ cycloalkyl, $C_1$-$C_6$ alkoxy, —CN, —CHO, acyl, phenyl, aryl or heteroaryl; or an N-oxide thereof or a pharmaceutically acceptable salt thereof or a prodrug thereof.

The compounds of the invention are estrogen receptor modulators useful in the treatment or inhibition of conditions, disorders, or disease states that are at least partially mediated by an estrogen deficiency or excess, or which may be treated or inhibited through the use of an estrogenic agent. Thus, in some aspects, the invention is directed to the use of the compounds of the invention in the treatment or prevention of diseases such as osteoporosis, inflammatory bowel diseases, Crohn's disease, ulcerative proctitis, colitis, estrogen dependent cancers, hypercholesteremia, hyperlipidemia, cardiovascular disease, atherosclerosis, senile dementias, Alzheimer's disease, anxiety disorders, neurodegenerative disorders, infertility, or arthritis.

DETAILED DESCRIPTION OF THE INVENTION

The present invention provides 6H-[1]benzopyrano[4,3-b]quinoline compounds, compositions containing the compounds, and methods for use of the compounds as estrogenic agents. The compounds of the invention are useful in the treatment and prevention of diseases associated with the estrogen receptor, particularly ERβ. In some embodiments, the estrogenic compounds of the invention have the formula I:

wherein:

A and A' are each independently OH, H or OR;

each R is independently selected from the group consisting of $C_1$-$C_6$ alkyl, alkenyl, benzyl, acyl, aroyl, —C(=O)—OR', sulfonyl and phosphoryl, wherein each R' is independently selected from $C_1$-$C_6$ alkyl, $C_2$-$C_7$ alkenyl, $C_2$-$C_7$ alkynyl, or $C_3$-$C_{10}$ cycloalkyl, each of which are optionally substituted by 1 to 3 substituents selected from $C_1$-$C_6$ alkyl or halogen;

$R^1$ and $R^2$ are independently selected from the group consisting of H, halogen, $C_1$-$C_6$ alkyl, $C_1$-$C_6$ perhaloalkyl, $CF_3$, $C_2$-$C_7$ alkenyl and $C_1$-$C_6$ alkoxy;

$R^3$, $R^4$, $R^5$ and $R^6$ are each independently selected from the group consisting of H, halogen, $CF_3$, $C_1$-$C_6$ perhaloalkyl, $C_1$-$C_6$ alkyl, $C_2$-$C_7$ alkenyl, $C_2$-$C_7$ alkyny -$C_7$ cycloalkyl, $C_1$-$C_6$ alkoxy, CN, —CHO, acyl, phenyl, aryl and heteroaryl;

wherein the alkyl or alkenyl moieties of $R^3$, $R^4$, $R^5$ and $R^6$ can each be optionally substituted with up to three substituents independently selected from halogen, OH, CN, trifluoroalkyl, trifluoroalkoxy, $NO_2$ or phenyl, wherein said phenyl is optionally substituted with up to three independently selected $R^{10}$ groups;

wherein the alkynyl moiety of $R^3$, $R^4$, $R^5$ and $R^6$ can each be optionally substituted with up to three substituents selected from halogen, —CN, —CHO, acyl, trifluoroalkyl, trialkylsilyl or phenyl, wherein said phenyl is optionally substituted with up to three independently selected $R^{10}$ groups;

wherein the phenyl, aryl or heteroaryl moiety of $R^3$, $R^4$, $R^5$ and $R^6$ can each be optionally substituted with up to three substituents selected from halogen, —CN, alkyl, alkoxy, perfluoroalkyl or perfluoroalkoxy;

each $R^{10}$ is independently selected from the group consisting of halogen, $C_1$-$C_6$ alkyl, $C_2$-$C_7$ alkenyl, —OH, $C_1$-$C_6$ alkoxy, —CN, —CHO, —$NO_2$, amino, $C_1$-$C_6$ alkylamino, di-($C_1$-$C_6$)alkylamino, thiol, and $C_1$-$C_6$ alkylthio; and n is 0, 1, 2, or 3; provided that:

at least one of A and A' is not H;

if n is 0, then $R_3$ is not halogen; and at least one of $R^3$, $R^4$ and $R^5$ is halogen, $C_1$-$C_6$ alkyl, $C_2$-$C_7$ alkenyl, $C_2$-$C_7$ alkynyl, $C_3$-$C_7$ cycloalkyl, $C_1$-$C_6$ alkoxy, —CN, —CHO, acyl, phenyl, aryl or heteroaryl; or an N-oxide thereof or a pharmaceutically acceptable salt thereof or a prodrug thereof.

In some embodiments, A and A' are each OH. In some further embodiments, one of A and A' is OH, and the other of A and A' is OR. In some further embodiments, one of A and A' is OH, and the other of A and A' is O—$C_1$-$C_6$ alkyl. In some further embodiments, A and A' are each OR. In still further embodiments, A and A' are each —O—$C_1$-$C_6$ alkyl. In still further embodiments, one of A and A' is H, and the other of A and A' is OH or OR. In further embodiments, one of A and A' is H, and the other of A and A' is OH or O—$C_1$-$C_6$ alkyl.

In some embodiments, $R^3$ and $R^5$ are each, independently, H, halogen, $C_1$-$C_6$ alkyl, $C_2$-$C_7$ alkenyl, $C_2$-$C_7$ alkynyl, —CN, —CHO, acyl or optionally substituted phenyl, as previously described. In some such embodiments, $R^3$ is other than H.

In some embodiments, $R^3$ is halogen, $C_1$-$C_6$ alkyl, $C_2$-$C_7$ alkenyl, $C_2$-$C_7$ alkynyl, —CN, —CHO, or phenyl optionally substituted with up to three groups selected from halogen, —O—$C_1$-$C_6$ alkyl (i.e., $C_1$-$C_6$ alkoxy), perfluoroalkyl and CN; and $R^5$ is H, halogen, $C_1$-$C_6$ alkyl, $C_2$-$C_7$ alkenyl, $C_2$-$C_7$ alkynyl, —CN, —CHO, or phenyl optionally substituted with up to three groups selected from halogen, $C_1$-$C_6$ alkoxy, perfluoroalkyl and CN. In some such embodiments, the phenyl of $R^3$ is optionally substituted with up to three substituents selected from F, Cl, Br, CN, $OCH_3$ and $CF_3$.

In some embodiments, $R^3$ is halogen, $C_2$-$C_7$ alkynyl or —CN. In some further embodiments, $R^3$ and $R^5$ are each independently halogen, $C_2$-$C_7$ alkynyl or —CN.

In some embodiments, one of $R^1$ and $R^2$ is halogen. In some preferred embodiments, one of $R^1$ and $R^2$ is fluorine. In some further embodiments, one of $R^1$ and $R^2$ is halogen, and the other of $R^1$ and $R^2$ is H. In some further embodiments, one of $R^1$ and $R^2$ is fluorine, and the other of $R^1$ and $R^2$ is H. In some further embodiments, $R^1$ and $R^2$ are each independently halogen. In some further embodiments, $R^1$ and $R^2$ are each fluorine. In some further embodiments, $R^1$ and $R^2$ are each H.

In some embodiments, $R^4$ is H, halogen or —CN, preferably H.

In some embodiments, $R^3$ is halogen, $C_1$-$C_6$ alkyl, $C_2$-$C_7$ alkenyl, $C_2$-$C_7$ alkynyl, —CN, —CHO, or phenyl optionally substituted with up to three groups selected from halogen, $C_1$-$C_6$ alkoxy, perfluoroalkyl and CN; $R^5$ is H, halogen, $C_1$-$C_6$ alkyl, $C_2$-$C_7$ alkenyl, $C_2$-$C_7$ alkynyl, —CN, —CHO, or phenyl optionally substituted with up to three groups selected from halogen, $C_1$-$C_6$ alkoxy, perfluoroalkyl and CN; and one of $R^1$ and $R^2$ is halogen; and $R^4$ is H, halogen or —CN.

In some embodiments, preferably those wherein A and A' are each OH, $R^1$, $R^2$, $R^4$, $R^5$ and $R^6$ are hydrogen, and $R^3$ is halogen, or $R^3$ is OH, or $R^3$ is $C_2$-$C_7$ alkenyl, or $R^3$ is CN, or $R^3$ is $C_2$-$C_7$ alkynyl, or $R^3$ is $C_1$-$C_6$ alkyl, or $R^3$ is optionally substituted phenyl, preferably wherein the substituents of the phenyl are halogen, $C_1$-$C_6$ alkoxy, perfluoroalkyl or CN.

In some embodiments of each of the foregoing, n is 1.

In some embodiments, the invention provides compositions containing one or more compounds of the invention, or pharmaceutically acceptable salts, chelates, complexes or prodrugs thereof.

It is to be understood that, when the compounds according to the present invention may be present either in their free base forms, as depicted in the formulae set forth herein, or as salts and/or hydrates thereof, and in particular as pharmaceutically acceptable salts thereof. Pharmaceutically acceptable salts are known in the art, as are hydrates, and the person having skill in the art will find it conventional to prepare such salts using art-recognized techniques. Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, naphthalenesulfonic, benzenesulfonic, toluenesulfonic, camphorsulfonic, and similarly known acceptable acids when a compound of this invention contains a basic moiety. Salts may also be formed from organic and inorganic bases, such as alkali metal salts (for example, sodium, lithium, or potassium), alkaline earth metal salts, ammonium salts, alkylammonium salts containing 1-6 carbon atoms or dialkylammonium salts containing 1-6 carbon atoms in each alkyl group, and trialkylammonium salts containing 1-6 carbon atoms in each alkyl group, when a compound of this invention contains an acidic moiety. Exemplary salts further include acid-addition salts, e.g., HCl, $H_2SO_4$, HBr, HI, $HNO_3$, $H_3PO_4$, $NaH_2PO_4$, $Na_2HPO_4$, $H_3PO_3$, $NaH_2PO_3$, $Na_2HPO_4$, $H_2SO_4$, $NaHSO_4$, carboxylic acids, such as acetic acid, malonic acid, capric acid, lauric acid, dichloroacetic acid, trichloroacetic acid, etc., and other pharmacologically tolerated salts. Hydrates include hemihydrates, monohydrates, dihydrates, etc. Unless otherwise modified herein, the use of a free base formula is intended to include the salt and/or hydrate thereof.

The instant invention also encompasses N-oxide derivatives of the compounds disclosed herein. These N-oxides can be prepared by methods known for preparing analogous compounds. For example, the compounds maybe oxidized with a peracid, hydrogen peroxide, an alkali metal peroxide or an alkyl peroxide. One useful N-oxide derivative is a composition where the nitrogen atom of the quinoline ring forms the N-oxide group.

The instant invention also encompasses prodrug derivatives. "Prodrug derivative" or "prodrug" means derivatives of the instant compounds that are converted in vivo to the corresponding non-derivatized form of the instant compounds.

The term "alkyl", as used herein, whether used alone or as part of another group, refers to an aliphatic hydrocarbon chain and includes, but is not limited to, straight and branched chains containing from 1 to 12 carbon atoms, preferably 1 to 6 carbon atoms, unless explicitly specified otherwise. For example, methyl, ethyl, propyl, isopropyl, butyl, isobutyl, tert-butyl, etc. are encompassed by the term "alkyl."

The number of carbon atoms as used in the definitions herein refers to the carbon backbone and carbon branching of the moiety, but does not include carbon atoms of the substituents, such as alkoxy substitutions and the like, of the moiety.

The term "alkenyl", as used herein, whether used alone or as part of another group, refers to an aliphatic hydrocarbon chain and includes, but is not limited to, straight and branched chains having 2 to 8 carbon atoms, e.g., 2-7 carbon atoms and containing at least one double bond. Preferably, the alkenyl moiety has 1 or 2 double bonds. For example, vinyl, allyl, 1-methyl vinyl, etc. are encompassed by the term "alkenyl". Such alkenyl moieties may exist in the E or Z conformations and the compounds of this invention include both conformations.

The term "alkynyl", as used herein, whether used alone or as part of another group, refers to an aliphatic hydrocarbon chain and includes, but is not limited to, straight and branched chains having 2 to 8 carbon atoms, e.g., 2-7 carbon atoms and containing at least one triple bond. Preferably, the alkynyl moiety has 1 or 2 triple bonds. For example, ethynyl, propynyl, etc. are encompassed by the term "alkynyl".

The term "acyl" refers to alkylcarbonyl groups, e.g., where alkyl is as defined herein. The term "benzyl" has its accustomed meaning as a phenylmethyl group. The term "aroyl" refers to an aryl moiety connected through a carbonyl group, such as a benzoyl group.

The alkyl, alkenyl, alkynyl, aryl, cycloalkyl, heteroaryl, aroyl, acyl and phenyl groups that are described herein for variables $R^1$, $R^2$, $R^3$, $R^4$, $R^5$, $R^6$, A and A' can be optionally substituted with one or more substituents, preferably, with up to three substituents. The substituents are independently selected, and include nitro, cyano, halo, hydroxy, carboxy, alkyl, alkenyl, alkynyl, cycloalkyl, aryl, heteroaryl, alkoxy, aryloxy, heteroaryloxy, alkylalkoxy, alkoxyalkoxy, perfluoroalkyl, perfluoroalkoxy, arylalkyl, alkylaryl, hydroxyalkyl, alkoxyalkyl, alkylthio, $S(O)_s$-aryl (where s=0-2) $S(O)_s$-heteroaryl (where s=0-2), or —C(=O)—OR', where R' is as previously described. In certain embodiments of the invention, preferred substituents include halogen, OH, CN, trifluoroalkyl, trifluoroalkoxy, perfluoroalkyl, perfluoroalkoxy, arylalkyl, alkylaryl, $NO_2$ and phenyl, wherein said phenyl is optionally substituted with up to three independently selected $R^{10}$ groups as described herein.

For example, when alkyl or alkenyl moieties are substituted, they can typically be mono-, di-, tri- or persubstituted. Examples for a halogen substituent include 1-bromo vinyl, 1-fluoro vinyl, 1,2-difluoro vinyl, 2,2-difluorovinyl, 1,2,2-trifluorovinyl, 1,2-dibromo ethane, 1,2-fluoro ethane, 1-fluoro-2-bromo ethane, $CF_2CF_3$, $CF_2CF_2CF_3$, and the like.

The term "halogen" includes fluorine, chlorine, bromine, and iodine.

Exemplary cycloalkyl groups include cyclopropyl, cyclobutyl, cyclopentyl, cyclohexyl, cycloheptyl, adamantyl, etc. In some embodiments, the cycloalkyl groups have 3-10 carbon atoms. Preferably cycloalkyl groups have 3-7 carbon atoms. As used herein, cycloalkyl further includes unsaturated cycloalkyl groups, i.e., cycloalkenyl groups. Exemplary unsaturated cycloalkyl groups include cyclopentenyl, cyclohexenyl, cycloheptenyl, etc.

Aryl groups are moieties that possess at least one aromatic ring containing no hetero (i.e., non-carbon) ring atoms. The term "aryl" includes mono- and polycyclic aromatic ring systems, e.g., of 6-15 carbon atoms, for example, phenyl, naphthyl, etc. Aryl groups can have fully or partially saturated rings fused to the aromatic ring. Thus, exemplary aryl groups include phenyl, naphthyl, pyrenyl, 5,6,7,8-tetrahydronaphth-1-yl, and the like.

The term heteroaryl is intended to mean an aromatic ring system that contains at least one non-carbon ring atom (e.g., one to three heteroatoms) selected from O, N and S and having for example five to 14 ring atoms. Exemplary heteroaryl groups include pyrrolyl, imidazolyl, pyridyl, pyrimidinyl, pyridazinyl, pyrazinyl, quinolyl, quoxalinyl, quinazolinyl, thiophenyl, furanyl, oxazolyl, thiazolyl, thienyl, pyranyl, thiopyranyl, benzofuranyl, indolyl, indazolyl, benzimidazolyl, benzothiazolyl, benzopyranyl, benzothiopyranyl, indazolyl, pyridopyrrolyl, and the like.

In some embodiments, the R' group of the —C(=O)—OR' moiety of A or A', is $C_1$-$C_6$ alkyl. In some embodiments, R' is $C_1$-$C_4$ alkyl. In some embodiments, the —C(=O)—OR' moiety is t-butoxycarbonyl (BOC).

As used in accordance with this invention, the term "providing," with respect to providing a compound or substance covered by this invention, means either directly administering such a compound or substance, or administering a prodrug, derivative, or analog that will form the effective amount of the compound or substance within the body.

Based on the results obtained in the standard pharmacological test procedure, as described below, the compounds of the invention are estrogen receptor modulators useful in the treatment or inhibition of conditions, disorders, or disease states that are at least partially mediated by an estrogen deficiency or excess, or which may be treated or inhibited through the use of an estrogenic agent. The compounds of this invention are particularly useful in treating a perimenopausal, menopausal, or postmenopausal patient in which the levels of endogenous estrogens produced are greatly diminished. Menopause is generally defined as the last natural menstrual period and is characterized by the cessation of ovarian function, leading to the substantial diminution of circulating estrogen in the bloodstream. As used herein, menopause also includes conditions of decreased estrogen production that may be caused surgically, chemically, or by a disease state that leads to premature diminution or cessation of ovarian function.

Accordingly, the compounds of this invention are useful in treating or inhibiting osteoporosis and in the inhibition of bone demineralization, which may result from an imbalance in formation of new bone tissues and the resorption of older tissues in an individual, leading to a net loss of bone. Such bone depletion results in a range of individuals, particularly in post-menopausal women, women who have undergone bilateral oophorectomy, those receiving or who have received extended corticosteroid therapies, those experiencing gonadal dysgenesis, and those suffering from Cushing's syndrome. Special needs for bone replacement, including teeth and oral bone, can also be addressed using these compounds in individuals with bone fractures, defective bone structures, and those receiving bone-related surgeries and/or the implantation of prosthesis. In addition to those problems described above, these compounds can be used in treatment or inhibition for osteoarthritis, spondyloarthropathies, hypocalcemia, hypercalcemia, Paget's disease, osteomalacia, osteohalisteresis, multiple myeloma and other forms of cancer having deleterious effects on bone tissues.

The compounds of this invention are further useful in treating or inhibiting joint damage secondary to arthroscopic or surgical procedures.

The compounds of this invention are also useful in treating or inhibiting benign or malignant abnormal tissue growth, including prostatic hypertrophy, uterine leiomyomas, breast cancer, endometriosis, endometrial cancer, polycystic ovary syndrome, endometrial polyps, benign breast disease, adenomyosis, ovarian cancer, melanoma, prostate cancer, cancers of the colon, CNS cancers, such as glioma or astioblastomia.

The compounds of this invention are cardioprotective and they are useful in lowering cholesterol, triglycerides, Lp(a) lipoprotein, and low density lipoprotein (LDL) levels; inhibiting or treating hypercholesteremia; hyperlipidemia; cardiovascular disease; atherosclerosis; peripheral vascular disease; restenosis, and vasospasm; and inhibiting vascular wall damage from cellular events leading toward immune mediated vascular damage. These cardiovascular protective properties are of great importance when treating postmenopausal patients with estrogens to inhibit osteoporosis and in the male when estrogen therapy is indicated.

The compounds of this invention are also antioxidants, and therefore, are useful in treating or inhibiting free radical induced disease states. Specific situations in which antioxidant therapy is indicated to be warranted are with cancers, central nervous system disorders, Alzheimer's disease, bone disease, aging, inflammatory disorders, peripheral vascular disease, rheumatoid arthritis, autoimmune diseases, respiratory distress, emphysema, asthma, pleurisy, uveitis, sepsis, hemorrhagic shock, prevention of reperfusion injury, viral hepatitis, chronic active hepatitis, tuberculosis, psoriasis, systemic lupus erythematosus, adult respiratory distress syndrome, central nervous system trauma and stroke.

The compounds of this invention are also useful in providing cognition enhancement, and in treating or inhibiting senile dementias, Alzheimer's disease, cognitive decline, neurodegenerative disorders, providing neuroprotection or cognition enhancement.

The compounds of this invention are also useful in treating or inhibiting inflammatory bowel disease, ulcerative proctitis, Crohn's disease, and colitis; menopausal related conditions, such as vasomotor symptoms, including hot flushes, vaginal or vulvar atrophy, atrophic vaginitis, vaginal dryness, pruritus, dyspareunia, dysuria, frequent urination, urinary incontinence, urinary tract infections, myalgia, arthralgia, insomnia, irritability, and the like; male pattern baldness; skin atrophy; acne; type II diabetes; dysfunctional uterine bleeding; and infertility.

The compounds of this invention are useful in disease states where amenorrhea is advantageous, such as leukemia, endometrial ablations, chronic renal or hepatic disease or coagulation diseases or disorders.

The compounds of this invention can be used as a contraceptive agent, particularly, when combined with a progestin.

When administered for the treatment or inhibition of a particular disease state or disorder, it is understood that the effective dosage may vary depending upon the particular compound utilized, the mode of administration, the condition being treated, and severity thereof, as well as, the various physical factors related to the individual being treated. Effective administration of the compounds of this invention may be given at an oral dose of from about 0.1 mg/day to about 1,000 mg/day. Preferably, administration will be from about 10 mg/day to about 600 mg/day, more preferably from about 50 mg/day to about 600 mg/day, in a single dose or in two or more divided doses. The projected daily dosages are expected to vary with route of administration.

Such doses may be administered in any manner useful in directing the active compounds herein to the recipient's bloodstream, including orally, via implants, parenterally (including intravenous, intraperitoneal and subcutaneous injections), rectally, intranasally, vaginally, and transdermally.

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g., corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Preferred surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidol silicon dioxide, phosphates, sodium dodecylsulfate, magnesium aluminum silicate, and triethanolamine. Oral formulations herein may utilize standard delay or time release formulations to alter the absorption of the active compound(s). The oral formulation may also consist of administering the active ingredient in water, or a fruit juice, containing appropriate solubilizers or emulsifiers, as needed.

In some cases, it may be desirable to administer the compounds directly to the airways in the form of an aerosol.

The compounds of this invention may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

For the purposes of this disclosure, transdermal administrations are understood to include all administrations across the surface of the body and the inner linings of bodily passages including epithelial and mucosal tissues. Such administrations may be carried out using the present compounds, N-oxides thereof, prodrugs thereof, or pharmaceutically acceptable salts thereof, in lotions, creams, foams, patches, suspensions, solutions, and suppositories (rectal and vaginal).

Transdermal administration may be accomplished through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquids or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semi-permeable membrane covering a reservoir containing the active ingredient with or without a carrier, or a matrix containing the active ingredient. Other occlusive devices are known in the literature.

Suppository formulations may be made from traditional materials, including cocoa butter, with or without the addition of waxes to alter the suppository's melting point, and glycerin. Water soluble suppository bases, such as polyethylene glycols of various molecular weights, may also be used.

Synthesis of Compounds of the Invention

The compounds of this invention can be prepared by methods known in the art of organic chemistry. The reagents used in the preparation of the compounds of this invention can be either commercially obtained or can be prepared by standard procedures described in the literature.

The syntheses of representative examples of this invention are described in the following Schemes 1-4. The Synthetic Methods A-M referred to in Schemes 1-4 are described in the Examples below.

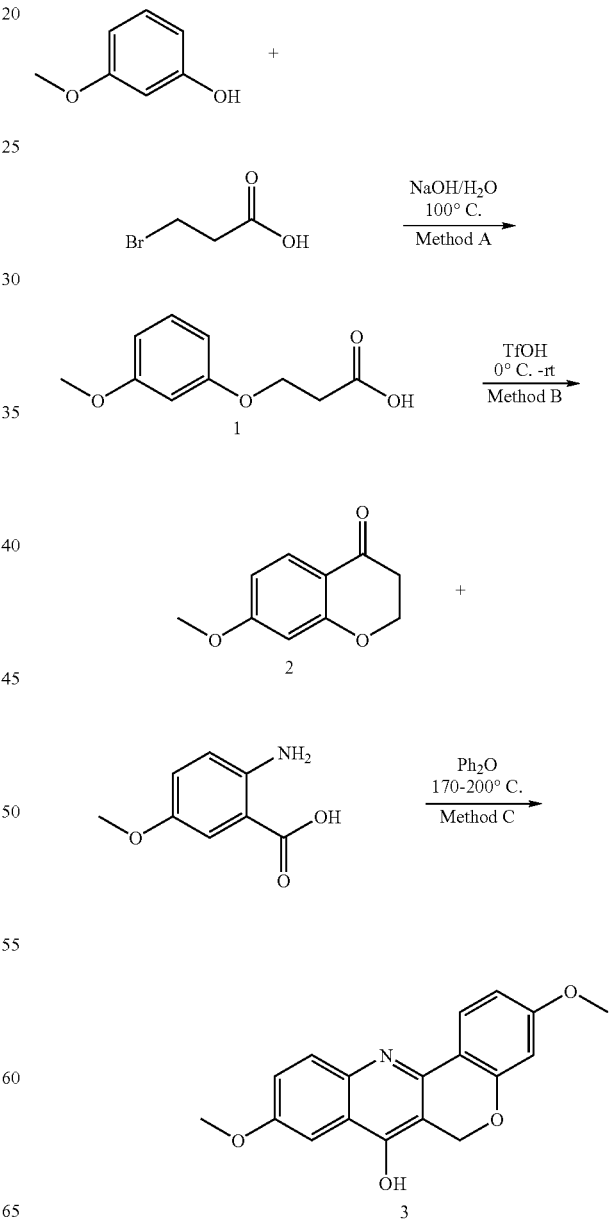

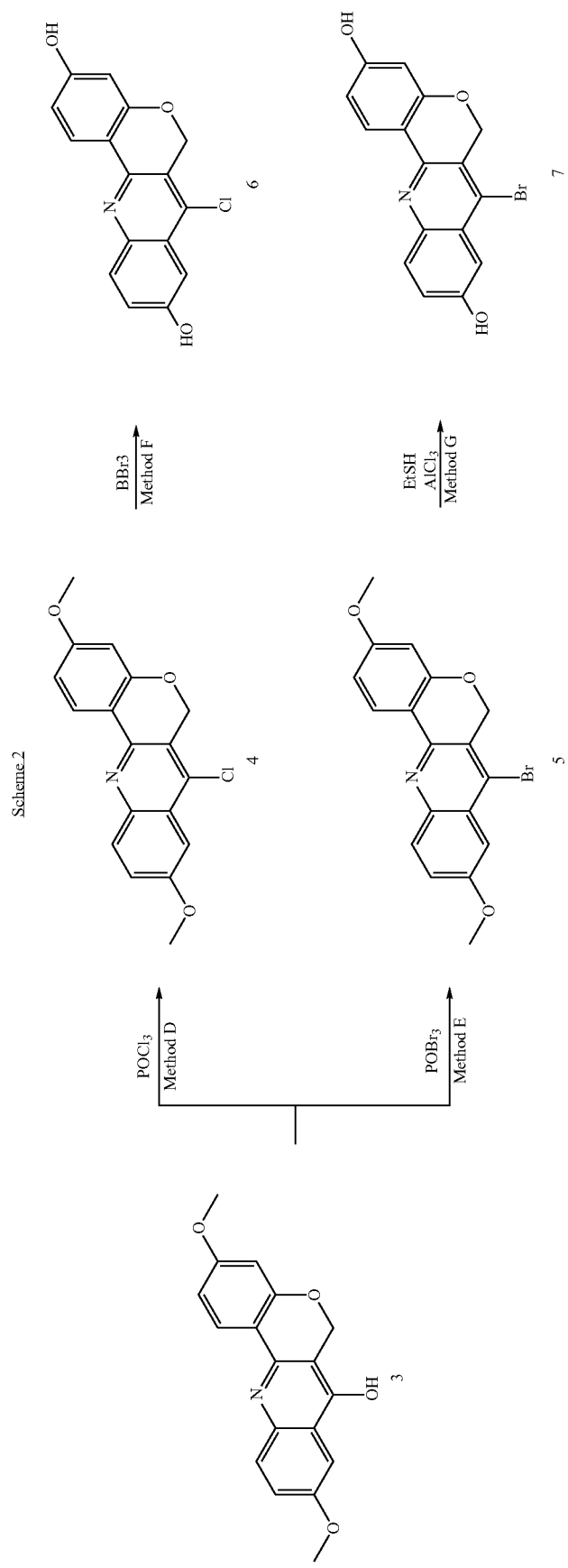

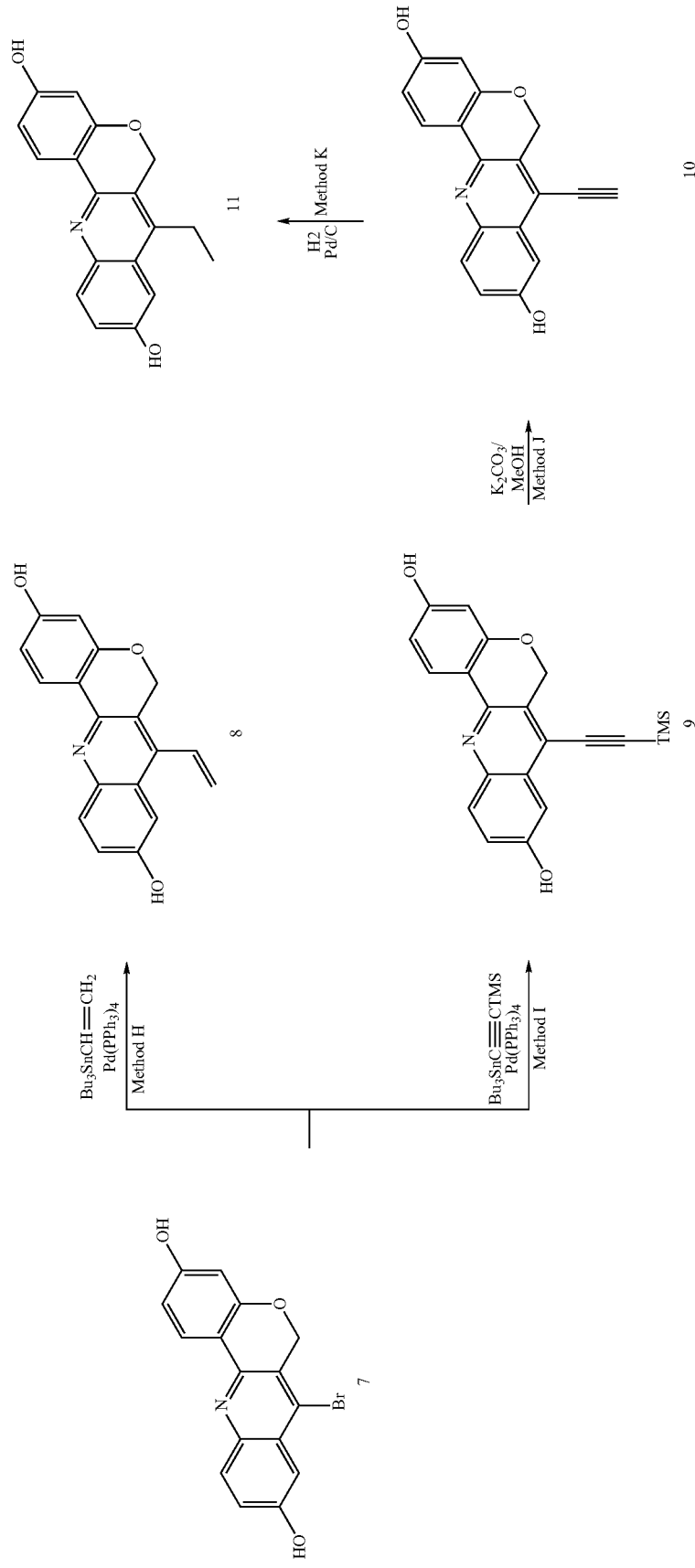

Scheme 4

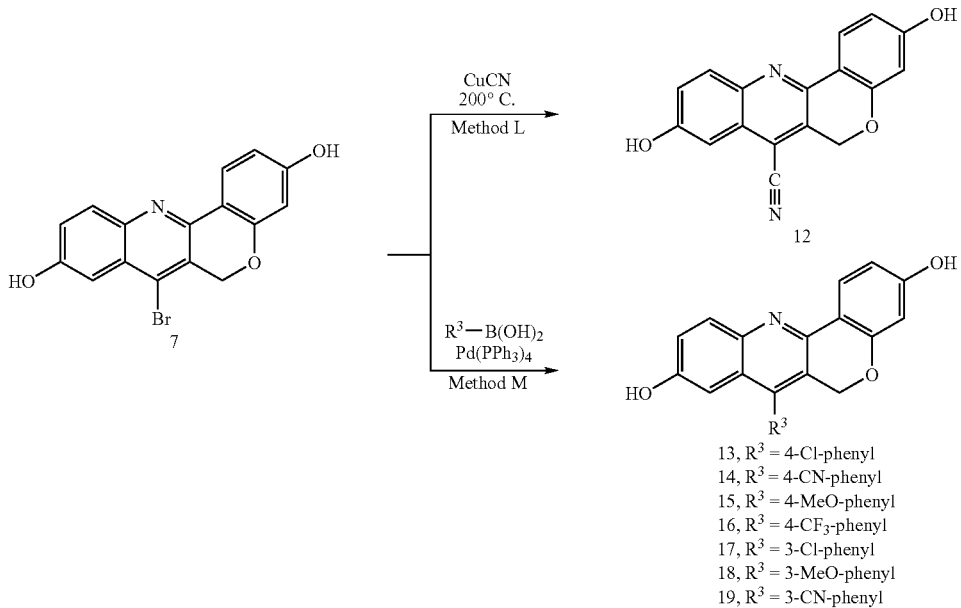

13, $R^3$ = 4-Cl-phenyl
14, $R^3$ = 4-CN-phenyl
15, $R^3$ = 4-MeO-phenyl
16, $R^3$ = 4-CF$_3$-phenyl
17, $R^3$ = 3-Cl-phenyl
18, $R^3$ = 3-MeO-phenyl
19, $R^3$ = 3-CN-phenyl

EXAMPLES

Synthesis of Representative Compounds of the Invention: General Method

Aldrich Sure Seal™ solvents, anhydrous without further purification, may be used for the reactions described herein and may be obtained from Aldrich Chemical Company (St. Louis, Mo.). All reactions were carried out under a nitrogen atmosphere. Chromatography was performed using 230-400 mesh silica gel (Merck Grade 60, Aldrich Chemical Company). Thin layer chromatography was performed with Silica Gel 60 F$_{254}$ plates from EM Science ( ). $^1$H and $^{19}$F NMR spectra were obtained on a Bruker AM-400 or Bruker DPX-300 instrument (Bruker, Billerica, Mass.) in deuterated solvents such as CDCl$_3$, DMSO-d6 or acetone-d6. Chemical shifts (δ) are given in parts per million (ppm) down field from tetramethylsilane (TMS). Melting points were determined on a Thomas-Hoover apparatus and are uncorrected. Infrared (IR) spectra were recorded on a Perkin-Elmer diffraction grating or Perkin-Elmer 784 spectrophotometers (Perkin-Elmer, Shelton, Conn.). Mass spectra were recorded on a Kratos MS 50 or Finnigan 8230 mass spectrometers. Compound nomenclature was generally arrived at by use of the Beilstein Autonom™ program.

Example 1

3-(3-METHOXY-PHENOXY)-PROPIONIC ACID (1)

Method A: To a mixture of 3-bromopropionic acid (14.70 g, 118 mmol) in water (100 mL) was added slowly NaHCO$_3$ (8.40 g, 100 mmol) and the resulting mixture was stirred for 5 mins. To this solution was added a 70-mL solution of 3-methoxyphenol (14.70 g, 96 mmol) in aqueous NaOH (4.67 g, 119 mmol), and the resulting mixture was heated at 100° C. for 3 hours. After cooling to room temperature, the reaction mixture was acidified with 1N HCl, and extracted with Et$_2$O. The Et$_2$O layer was washed with aqueous NaHCO$_3$ (3×). The aqueous layer was again acidified with 1N HCl and extracted with Et$_2$O. The Et$_2$O layer was washed with water, brine, dried (Na$_2$SO$_4$), filtered and concentrated to give a crude brown solid, which was recrystallized (Et$_2$O/−20° C.) to give a pure product as a yellow solid. Yield: 17.0 g (23%). $^1$H-NMR (300 MHz, CDCl$_3$): δ 2.85 (t, J=6.3 Hz, 2H), 3.79 (s, 3H), 4.24 (t, J=6.3 Hz, 2H), 6.50 (m, 3H), 7.18 (t, J=8.2 Hz, 1H), 11.45 (br, 1H); MS (ESI) m/z 195 ([M−H]$^−$); Anal. Calcd for C$_{10}$H$_{12}$O$_4$: C, 61.22; H, 6.16. Found: C, 61.24; H, 6.12

Example 2

7-METHOXY-COROMAN-4-ONE (2)

Method B: To a reaction vessel containing 3-(3-methoxyphenoxy)-propionic acid (1) (7.00 g, 35.6 mmol) at 0° C. was added slowly trifluoromethanesulfonic acid (15 mL). The reaction mixture was stirred for 3 hours while allowing to warm up to room temperature. After cooling to 0° C., the reaction mixture was quenched with crushed ice, then extracted with Et$_2$O (2×300 mL). The organic layer was washed with water (2×), aqueous NaHCO$_3$, water, brine, then dried (Na$_2$SO$_4$), filtered and concentrated to give a crude oil, which was purified by silica gel chromatography to give a pure product as a yellow solid. Yield: 4.26 g (67%). $^1$H-NMR (300 MHz, CDCl$_3$): δ 2.76 (t, J=6.3 Hz, 2H), 3.84 (s, 3H), 4.52 (t, J=6.3 Hz, 2H), 6.41 (d, J=2.3 Hz, 1H), 6.58 (dd, J=8.8, 2.3 Hz, 1H), 7.84 (d, J=8.8 Hz, 1H); MS (ESI) m/z 179 ([M+H]$^+$).

Example 3

3,9-DIMETHOXY-6H-CHROMENO[4,3-b] QUINOLIN-7-OL (3)

Method C: A mixture of 2-amino-5-methoxybenzoic acid (1.839 g, 11.00 mmol) and 7-methoxy-chroman-4-one (2)

(1.960 g, 11.00 mmol) in Ph$_2$O (10 mL) was heated at 170° C. for 1 hour and at 200° C. for 7 hours. After cooling to room temperature, hexane was added. The yellow precipitate formed was collected by filtration and washed successfully with hexane and Et$_2$O and dried in vacuo. Yield: 2.171 g (64%). mp 298° C. (dec.); $^1$H-NMR (300 MHz, DMSO-d$_6$) δ 3.82 (s, 3H), 3.84 (s, 3H), 5.17 (s, 2H), 6.64 (d, J=2.4 Hz, 1H), 6.79 (dd, J=8.7, 2.4 Hz, 1H), 7.31 (dd, J=9.0, 2.9 Hz, 1H), 7.50 (d, J=2.8 Hz, 1H), 7.74 (d, J=9.0 Hz, 1H), 7.99 (d, J=8.7 Hz, 1H), 11.56 (s, 1H); MS (ESI) m/z 308 ([M−H]$^−$), 310 ([M+H]$^+$); HRMS (ESI$^+$) calcd for C$_{18}$H$_{15}$NO$_4$ 310.1074 ([M+H]$^+$), Found: 310.1068.

Example 4

7-CHLORO-3,9-DIMETHOXY-6H-CHROMENO [4,3-b]QUINOLINE (4)

Method C: A mixture of 3,9-dimethoxy-6H-chromeno[4, 3-b]quinolin-7-ol (3) (124 mg, 0.400 mmol) and POCl$_3$ (1 mL) was heated at reflux for 1 hour. After cooling, excess POCl$_3$ was removed under reduced pressure. Water and then aqueous K$_2$CO$_3$ were slowly added to the solid residue and the reaction mixture was extracted with EtOAc. The organic layer was washed with brine, then dried (Na$_2$SO$_4$), filtered and concentrated to give a crude solid, which was passed through a short pad of silica gel and recrystallized (hot heptane/−20° C.) to give a pure product as a yellow powder. Yield: 124 mg (95%); mp 190-191° C.; $^1$H-NMR (300 MHz, CDCl$_3$) δ 3.85 (s, 3H), 3.97 (s, 3H), 5.50 (s, 2H), 6.53 (d, J=2.4 Hz, 1H), 6.71 (dd, J=8.7, 2.4 Hz, 1H), 7.35 (dd, J=8.9, 2.8 Hz, 1H), 7.38 (d, J=3.2 Hz, 1H), 7.98 (d, J=8.8 Hz, 1H), 8.29 (d, J=8.7 Hz, 1H); MS (ESI) m/z 328/330 ([M+H]$^+$); HRMS (ESI$^+$) calcd for C$_{18}$H$_{14}$ClNO$_3$ 328.0735 ([M+H]$^+$). Found: 328.0728; Anal. calcd for C$_{18}$H$_{14}$ClNO$_3$: C:65.96, H: 4.31, N: 4.27. Found: C: 65.71, H: 4.17, N: 3.92.

Example 5

7-BROMO-3,9-DIMETHOXY-6H-CHROMENO [4,3-b]QUINOLINE (5)

Method E. A mixture of 3,9-dimethoxy-6H-chromeno[4, 3-b]quinolin-7-ol (3) (1.025 g, 3.31 mmol) and POBr$_3$ (1.430 g, 5.00 mmol, 1.5 equiv.) in DMF (15 mL) was heated at 70° C. for 30 mins. After cooling to room temperature, water and then aqueous K$_2$CO$_3$ were slowly added, and the reaction mixture was extracted with warm CHCl$_3$ (2×). The organic layer was washed with water (2×) and brine, then dried (Na$_2$SO$_4$), filtered through a short pad of silica gel and concentrated to give a crude yellow solid, which was recrystallized (hot EtOAc/−20° C.) to give a pure product as yellow needles. Yield: 1.127 g (91%); mp 196-197° C.; $^1$H-NMR (300 MHz, CDCl$_3$) δ 3.85 (s, 3H), 3.98 (s, 3H), 5.48 (s, 2H), 6.53 (d, J=2.4 Hz, 1H), 6.71 (dd, J=8.7, 2.5 Hz, 1H), 7.35 (dd, J=9.0, 2.7 Hz, 1H), 7.39 (d, J=2.7 Hz, 1H), 7.97 (d, J=9.0 Hz, 1H), 8.30 (d, J=8.7 Hz, 1H); MS (ESI) m/z 372/374 ([M+H]$^+$); HRMS (ESI$^+$) calcd for C$_{18}$H$_{14}$BrNO$_3$ 372.0230 ([M+H]$^+$). Found: 372.0228; Anal. calcd for C$_{18}$H$_{14}$BrNO$_3$: C, 58.08, H, 3.79, N, 3.76. Found: C, 57.94, H, 3.68, N, 3.73.

Example 6

7-CHLORO-3,9-DIHYDROXY-6H-CHROMENO [4,3-b]QUINOLINE (6)

Method F: To a solution of 7-chloro-3,9-dimethoxy-6H-chromeno[4,3-b]quinoline (4) (68 mg, 0.21 mmol) in 1,2-dichloroethane (3 mL) was added slowly a solution of BBr$_3$ (1.0 M, 1 mL, 1 mmol) in CH$_2$Cl$_2$. The reaction mixture was stirred at room temperature for 30 mins. and then at 40° C. for 2 hours. After cooling in an ice bath, aqueous NaHCO$_3$ was added very slowly with vigorous stirring to quench the reaction, and the resulting reaction mixture was extracted with EtOAc. The organic layer was washed with brine, then dried (Na$_2$SO$_4$), filtered through a short pad of silica gel, and concentrated to give a yellow solid, which was recrystallized (THF/hexane). Yield: 56 mg (90%); mp 235° C. (dec.); $^1$H-NMR (300 MHz, DMSO-d6) δ 5.47 (s, 2H), 6.40 (s, 1H), 6.60 (d, J=8.0 Hz, 1H), 7.34 (d, J=2.1 Hz, 2 H), 7.89 (d, J=9.6 Hz, 1H), 8.09 (d, J=8.6 Hz, 1H), 10.10 (s, 1H), 10.35 (s, 1H); HRMS (ESI$^+$) calcd for C$_{16}$H$_{10}$ClNO$_3$ 300.0422 ([M+H]$^+$). Found: 300.0411.

Example 7

7-BROMO-3,9-DIHYDROXY-6H-CHROMENO [4,3-b]QUINOLINE (7)

Method G: To a solution of 7-bromo-3,9-dimethoxy-6H-chromeno[4,3-b]quinoline (5) (881 mg, 2.37 mmol) in 1,2-dichloroethane (20 mL) was added slowly AlCl$_3$ (3.16 g, 23.7 mmol) and EtSH (2.7 mL, 36 mmol) and the reaction mixture was stirred at room temperature for 3 hours. After cooling in an ice bath, aqueous NaHCO$_3$ was added very slowly with vigorous stirring to quench the reaction, and the resulting reaction mixture was extracted with EtOAc. The precipitate formed was filtered through Celite®. The organic layer was washed with brine, then dried (Na$_2$SO$_4$), filtered and concentrated to give a crude yellow solid, which was purified by silica gel chromatography to give a pure product as an orange solid. Yield: 478 mg (59%); mp 240° C. (dec.); $^1$H-NMR (300 MHz, DMSO-d6) δ 5.44 (s, 2H), 6.41 (d, J=2.3 Hz, 1H), 6.59 (dd, J=8.6, 2.3 Hz, 1H), 7.33 (dd, J=8.7, 2.6 Hz, 1H), 7.35 (s, 1H), 7.88 (d, J=8.7 Hz, 1H), 8.09 (d, J=8.6 Hz, 1H), 10.09 (s, 1H), 10.35 (s, 1H); MS (ESI) m/z 342/344 ([M−H]$^−$), 344/346 ([M+H]$^+$); HRMS (ESI$^+$) calcd for C$_{16}$H$_{10}$BrN—O$_3$ 343.9917 ([M+H]$^+$). Found: 343.9911.

Example 8

3,9-DIHYDROXY-7-VINYL-6H-CHROMENO [4,3-b]QUINOLINE (8)

Method H: A mixture of 7-bromo-3,9-dihydroxy-6H-chromeno[4,3-b]quinoline (7) (34.5 mg, 0.100 mmol), tributyl(vinyl)tin (38 mg, 0.120 mmol, 1.2 equiv.), and Pd(PPh$_3$)$_4$ (11.6 mg, 0.0100 mmol, 10 mol %) in toluene (1.5 mL) was refluxed under nitrogen until all starting material was consumed (1-2 hour(s)). Filtration through Celite® and purification by passing through a short pad of silica gel gave a pure product as an orange powder. Yield: 24 mg (83%); mp 160° C. (dec.); $^1$H-NMR (400 MHz, DMSOd-6) δ 5.36 (s, 2H), 5.47 (dd, J=17.9, 1.4 Hz, 1H), 5.91 (dd, J=11.6, 1.4 Hz, 1H), 6.38 (d, J=2.3 Hz, 1H), 6.58 (dd, J=8.5, 2.3 Hz, 1H), 7.10 (dd, J=17.7, 11.6 Hz, 1H), 7.22 (d, J=2.5 Hz, 1H), 7.26 (dd, J=9.1, 2.6 Hz, 1H), 7.84 (d, J=J=8.9 Hz, 1H), 8.10 (d, J=8.5 Hz, 1H), 9.94 (s, 1H), 9.95 (s, 1H); MS (ESI) m/z 290

([M−H]⁻), 292 ([M+H]⁺); HRMS (ESI⁺) calcd for $C_{18}H_{13}NO_3$ 292.0968 ([M+H]⁺). Found: 292.0962.

Example 9

3,9-DIHYDROXY-7-[(TRIMETHYLSILYL)ETHYNYL]-6H-CHROMENO[4,3-b]QUINOLINE (9)

Method I: A mixture of 7-bromo-3,9-dihydroxy-6H-chromeno[4,3-b]quinoline (7) (51.6 mg, 0.150 mmol), (trimethylsilylethynyl)tributyltin (70 mg, 0.180 mmol, 1.2 equiv.), and Pd(PPh₃)₄ (17 mg, 0.015 mmol, 10 mol %) in toluene (2 mL) was refluxed under nitrogen until all starting material was consumed (1-2 hour(s)). Filtration through Celite® and purification by passing through a short pad of silica gel gave a pure product as a red solid. Yield: 54 mg (99.6%); mp 160° C. (dec.); ¹H-NMR (300 MHz, acetone-d6) δ 0.43 (s, 9H), 5.53 (s, 2H), 6.52 (d, J=2.3 Hz, 1H), 6.71 (dd, J=8.6, 2.3 Hz, 1H), 7.42 (dd, J=9.1, 2.7 Hz, 1H), 7.61 (d, J=2.7 Hz, 1H), 7.97 (d, J=9.0 Hz, 1H), 8.26 (d, J=8.6 Hz, 1H), 8.94 (s, 1H), 9.16 (s, 1H); MS (ESI) m/z 360 ([M−H]⁻), 362 ([M+H]⁺); HRMS (ESI⁺) calcd for $C_{21}H_{19}NO_3Si$ 362.1207 ([M+H]³⁰). Found: 362.1207.

Example 10

3,9-DIHYDROXY-7-ETHYNYL-6H-CHROMENO[4,3-b]QUINOLINE (10)

Method J: To a solution of 3,9-dihydroxy-7-[(trimethylsilyl)ethynyl]-6H-chromeno[4,3-b]quinoline (9) (54 mg, 0.15 mmol) in MeOH (2 mL) was added K₂CO₃ (104 mg, 0.75 mmol, 5 equiv.) and the reaction mixture was stirred for 30 mins. at room temperature. The reaction mixture was quenched with aqueous NH₄Cl (5 mL). Methanol (MeOH) was removed under reduced pressure and the reaction mixture was extracted with EtOAc. The organic layer was washed with water and brine, then dried (Na₂SO₄), filtered and concentrated to give a crude yellow solid, which was purified by passing through a short pad of silica gel to give a pure product as a burgundy powder. Yield: 27 mg (63%); mp 220° C. (dec.); ¹H-NMR (300 MHz, DMSOd-6) δ 5.27 (s, 1H), 5.46 (s, 2H), 6.41 (d, J=2.1 Hz, 1H), 6.59 (dd, J=8.5, 2.1 Hz, 1H), 7.31 (dd, J=9.1, 2.6 Hz, 1H), 7.41 (d, J=2.5 Hz, 1H), 7.87 (d, J=9.0 Hz, 1H), 8.09 (d, J=8.5 Hz, 1H), 10.04 (s, 1H), 10.23 (s, 1H); MS (ESI) m/z 288 ([M−H]⁻), 290 ([M+H]⁺); HRMS (ESI⁺) calcd for $C_{18}H_{11}NO_3$ 290.0812 ([M+H⁺]. Found: 290.0808.

Example 11

3,9-DIHYDROXY-7-ETHYL-6H-CHROMENO[4,3-b]QUINOLINE (11)

Method K: A mixture of 3,9-dihydroxy-7-ethynyl-6H-chromeno[4,3-b]quinoline (10) (13 mg, 0.045 mmol) and Pd/C (10 wt. %) in EtOAc/THF (1.5 mL) was stirred under hydrogen atmosphere (1 atm, balloon) for 30 mins. The reaction mixture was filtered through Celite®, and concentrated to give a yellow solid, which was recrystallized (EtOAc/hexane/−20° C.). Yield: 13 mg (98%). mp 145° C. (dec.); ¹H-NMR (300 MHz, DMSOd-6) δ 1.18 (t, J=7.4 Hz, 3H), 2.95 (q, J=7.6 Hz, 2H), 5.41 (s, 2H), 6.38 (d, J=2.2 Hz, 1H), 6.56 (dd, J=8.5, 2.3 Hz, 1H), 7.24 (dd, J=8.3, 2.4 Hz, 1H), 7.26 (s, 1H), 7.82 (d, J=9.0 Hz, 1H), 8.09 (d, J=8.5 Hz, 1H), 9.90 (s, 1H), 9.93 (s, 1H); MS (ESI) m/z 292 ([M−H]⁻), 294 ([M+H]⁺); HRMS (ESI⁺) calcd for $C_{18}H_{15}NO_3$ 294.1125 ([M+H]⁺). Found: 294.1123.

Example 12

7-CYANO-3,9-DIHYDROXY-6H-CHROMENO[4,3-b]QUINOLINE (12)

Method L: A mixture of 7-bromo-3,9-dihydroxy-6H-chromeno[4,3-b]quinoline (7) (47 mg, 0.14 mmol), CuCN (370 mg, 4.13 mmol) in anhydrous DMF (2 mL) was heated at 200° C. in a sealed tube until all starting material was consumed (5 hours). After cooling to room temperature, the reaction mixture was filtered through Celite® and rinsed with EtOAc. Water was added to the filtrate and the reaction mixture was extracted with EtOAc. The organic layer was washed with water (2×) and brine, then dried (Na₂SO₄), filtered and concentrated to give a crude solid, which was purified by silica gel chromatography to give a pure product as a brown powder. Yield: 9 mg (23%); ¹H-NMR (300 MHz, DMSOd-6) δ 5.52 (s, 2H), 6.44 (d, J=2.1 Hz, 1H), 6.6 (dd, J=8.6, 2.1 Hz, 1H), 7.27 (d, J=2.4 Hz, 1H), 7.41 (dd, J=9.1, 2.5 Hz, 1H), 7.98 (d, J=9.1 Hz, 1H), 8.09 (d, J=8.6 Hz, 1H), 10.19 (s, 1H), 10.63 (s, 1H); MS (ESI) m/z 289 ([M−H]⁻), 291 ([M+H]⁺); HRMS (ESI⁺) calcd for $C_{17}H_{10}N_2O_3$ 291.0764 ([M+H]⁺). Found: 291.0758.

Example 13

7-(4-CHLOROPHENYL)-3,9-DIHYDROXY-6H-CHROMENO[4,3-b]QUINOLINE (13)

Method M. A mixture of 7-bromo-3,9-dihydroxy-6H-chromeno[4,3-b]quinoline (7) (40 mg, 0.12 mmol) and Pd(PPh₃)₄ (7 mg, 0.006 mmol, 5 mol %) in DME (3 mL) was stirred for 10 mins. at room temperature. To this mixture were added sequentially 4-chlorophenylboronic acid (22 mg, 0.14 mmol, 1.2 equiv.) and aqueous Na₂CO₃ (2 M soln, 5 equiv.), and the reaction mixture was refluxed until all starting material was consumed (2-3 hours). After cooling, aqueous NH₄Cl was added and the reaction mixture extracted with EtOAc. The organic layer was washed with water and brine, then dried (Na₂SO₄), filtered and concentrated to give a crude solid, which was purified by passing through a short pad of silica gel to give a pure product as a red powder. Yield: 41 mg (94%); mp 215-218° C. (dec.); ¹H-NMR (400 MHz, DMSOd-6) δ 5.01 (s, 2H), 6.36 (d, J=2.2 Hz, 1H), 6.60 (dd, J=8.7, 2.2 Hz, 1H), 6.62 (d, J=2.5 Hz, 1H), 7.26 (dd, J=9.1, 2.6 Hz, 1H), 7.41 (d, J=8.4 Hz, 2H), 7.68 (d, J=8.4 Hz, 2H), 7.90 (d, J=9.0 Hz, 1H), 8.15 (d, J=8.4 Hz, 1H), 9.82 (s, 1H), 9.98 (s, 1H); MS (ESI) m/z 374/376 ([M−H]⁻), 376/378 ([M+H]⁺); HRMS (ESI⁺) calcd for $C_{22}H_{14}ClNO_3$ 376.0735 ([M+H]⁺). Found: 376.0728.

Example 14

7-(4-CYANOPHENYL)-3,9-DIHYDROXY-6H-CHROMENO[4,3-b]QUINOLINE (14)

This compound was prepared from 7-bromo-3,9-dihydroxy-6H-chromeno[4,3-b]quinoline (7) using 4-cyanophenylboronic acid according to method M. Ivory powder; Yield: 96%; mp 295° C. (dec.); ¹H-NMR (400 MHz, DMSOd-6) δ 4.99 (s, 2H), 6.36 (d, J=2.3 Hz, 1H), 6.53 (d, J=2.7 Hz, 1H), 6.61 (dd, J=8.7, 2.3 Hz, 1H), 7.27 (dd, J=9.1, 2.6 Hz, 1H), 7.62 (d, J=8.5 Hz, 2H), 7.91 (d, J=9.0 Hz, 2H), 8.09 (d, J=8.3 Hz, 1H), 8.16 (d, J=8.6 Hz, 1H), 9.86 (s, 1H), 9.99 (s, 1H); MS (ESI) m/z 365 ([M−H]⁻), 367 ([M+H]⁺); HRMS (ESI⁺) calcd for $C_{23}H_{14}N_2O_3$ 367.1077 ([M+H]³⁰). Found: 367.1074.

Example 15

3,9-DIHYDROXY-7-(4-METHOXYPHENYL)-6H-CHROMENO[4,3-b]QUINOLINE (15)

This compound was prepared from 7-bromo-3,9-dihydroxy-6H-chromeno[4,3-b]quinoline (7) using 4-methoxyphenylboronic acid according to method M. Yellow powder; Yield: 84%; mp 195° C. (dec.); $^1$H-NMR (400 MHz, DMSOd-6) δ 3.87 (s, 3H), 5.03 (s, 2H), 6.36 (d, J=2.2 Hz, 1H), 6.60 (dd, J=8.5, 2.5 Hz, 1H), 6.73 (d, J=8.6 2.6 Hz, 1H), 7.16 (d, J=8.6 Hz, 2H), 7.24 (dd, J=9.0, 2.6 Hz, 1H), 7.30 (d, J=8.6 Hz, 2H), 7.89 (d, J=9.0 Hz, 1H), 8.15 (d, J=8.6 Hz, 1H), 9.80 (s, 1H), 9.98 (s, 1H); MS (ESI) m/z 370 ([M−H]$^-$), 372 ([M+H]$^+$); HRMS (ESI$^+$) calcd for $C_{23}H_{17}NO_4$ 372.1230 ([M+H]$^+$). Found: 372.1226.

Example 16

3,9-DIHYDROXY-7-[4-(TRIFLUOROMETHYL)PHENYL]-6H-CHROMENO[4,3-b]QUINOLINE (16)

This compound was prepared from 7-bromo-3,9-dihydroxy-6H-chromeno[4,3-b]quinoline (7) using 4-trifluoromethylphenylboronic acid according to method M. Yellow powder; Yield: 95%; mp 175-177° C. (dec.); $^1$H-NMR (400 MHz, DMSOd-6) δ 5.00 (s, 2H), 6.36 (d, J=2.3 Hz, 1H), 6.56 (d, J=2.6 Hz, 1H), 6.61 (dd, J=8.6, 2.2 Hz, 1H), 7.26 (dd, J=9.1, 2.6 Hz, 1H), 7.64 (d, J=7.9 Hz, 2H), 7.92 (d, J=9.0 Hz, 1H), 7.98 (d, J=8.1 Hz, 2H), 8.16 (d, J=8.6 Hz, 1H), 9.84 (s, 1H), 10.00 (s, 1H); $^{19}$F-NMR (400 MHz, DMSOd-6) δ −61.43 (s); MS (ESI) m/z 408 ([M−H]$^-$), 410 ([M+H]$^+$); HRMS (ESI$^+$) calcd for $C_{23}H_{14}F_3NO_3$ 410.0999 ([M+H]$^+$). Found: 410.0992.

Example 17

7-(3-CHLOROPHENYL)-3,9-DIHYDROXY-6H-CHROMENO[4,3-b]QUINOLINE (17)

This compound was prepared from 7-bromo-3,9-dihydroxy-6H-chromeno[4,3-b]quinoline (7) using 3-chlorophenylboronic acid according to method M. Orange powder; Yield: 94%; mp 162-165° C. (dec.); $^1$H-NMR (400 MHz, DMSOd-6) δ 5.01 (s, 2H), 6.36 (d, J=2.3 Hz, 1H), 6.60 (dd, J=8.5, 2.2 Hz, 1H), 6.61 (d, J=2.6 Hz, 1H), 7.26 (dd, J=9.1, 2.6 Hz, 1H), 7.35 (m, 1H), 7.50 (d, J=1.0 Hz, 1H), 7.64 (dd, J=3.9, 1.6, Hz, 2H), 7.90 (d, J=9.1 Hz, 1H), 8.15 (d, J=8.8 Hz, 1H), 9.86 (s, 1H), 9.98 (s, 1H); MS (ESI) m/z 374/376 ([M−H]$^-$), 376/378 ([M+H]$^+$); HRMS (ESI+) calcd for $C_{22}H_{14}ClNO_3$ 376.0735 ([M+H]$^+$). Found: 376.0721.

Example 18

3,9-DIHYDROXY-7-(3-METHOXYPHENYL)-6H-CHROMENO[4,3-b]QUINOLINE (18)

This compound was prepared from 7-bromo-3,9-dihydroxy-6H-chromeno[4,3-b]quinoline (7) using 3-methoxyphenylboronic acid according to method M. Yellow powder; Yield: 87%; mp 155-158° C. (dec.); $^1$H-NMR (400 MHz, DMSOd-6) δ 3.82 (s, 3H), 4.99 (d, J=14.2 Hz, 1H), 5.04 (d, J=14.2 Hz, 1H), 6.35 (d, J=2.3 Hz, 1H), 6.60 (dd, J=8.6, 2.3 Hz, 1H), 6.71 (d, J=2.7 Hz, 1H), 6.90 (m, 1H), 6.92 (d, J=1.6 Hz, 1H), 7.12 (m, 1H), 7.24 (dd, J=9.1, 2.7 Hz, 1H), 7.52 (dd, J=8.2, 7.9 Hz, 1H), 7.89 (d, J=9.1 Hz, 1H), 8.15 (d, J=8.6 Hz, 1H), 9.80 (s, 1H), 9.96 (s, 1H); MS (ESI) m/z 370 ([M−H]$^-$), 372 ([M+H]$^+$); HRMS (ESI$^+$) calcd for $C_{23}H_{17}NO_4$ 372.1230 ([M+H]$^+$). Found: 372.1223.

Example 19

7-(3-CYANOPHENYL)-3,9-DIHYDROXY-6H-CHROMENO[4,3-b]QUINOLINE (19)

This compound was prepared from 7-bromo-3,9-dihydroxy-6H-chromeno[4,3-b]quinoline (7) using 3-cyanophenylboronic acid according to method M. Yellow powder; Yield: 74%; mp 275° C. (dec.); $^1$H-NMR (400 MHz, DMSOd-6) δ 4.98 (d, J=14.2 Hz, 1H), 5.03 (d, J=14.2 Hz, 1H), 6.36 (d, J=2.3 Hz, 1H), 6.54 (d, J=2.6 Hz, 1H), 6.61 (dd, J=8.6, 2.3 Hz, 1H), 7.27 (dd, J=9.1, 2.6 Hz, 1H), 7.74 (dt, J=7.8, 1.4 Hz, 1H), 7.82 (t, J=7.7 Hz, 1H), 7.92 (d, J=9.1 Hz, 1H), 7.94 (d, J=1.6 Hz, 1H), 8.05 (dt, J=7.7, 1.4 Hz, 1H), 8.16 (d, J=8.6 Hz, 1H), 9.87 (s, 1H), 10.00 (s, 1H); MS (ESI) m/z 365 ([M−H]$^-$), 367 ([M+H]$^+$); HRMS (ESI$^+$) calcd for $C_{23}H_{14}N_2O_3$ 367.1066 ([M+H]$^+$). Found: 367.1083.

Pharmacological Test Procedures

Demonstration of Estrogenic Activity

Representative examples of the invention were evaluated for their ability to compete with 17β-estradiol for both ERα and ERβ. The test procedure used allows one to determine whether a particular compound binds to the estrogen receptor (and is therefore "estrogenic") and whether there is selectivity for ERα or ERβ. Results of representative compound examples are shown in Table 1 below, with the values obtained reported as $IC_{50}$s. The $IC_{50}$ is defined as the concentration of compound that decreases total 17β-estradiol binding by 50%. The procedure used is briefly described. A crude lysate of *E. coli* expressing the estrogen receptor ligand binding domains (D, E, and F) of human ERα or ERβ was prepared. Both receptors and compounds were diluted in 1× Dulbecco's phosphate buffered saline (DPBS) supplemented with 1 mM ethylenediamine tetraacetic acid (EDTA). Using a high binding masked microtiter plate, 100 uL of receptor (1 uG/well) was combined with 2 nM [$^3$H]-17β-estradiol and various concentrations of compound. After between 5 and 15 hours at room temperature, the plates were washed with DPBS/1 mM EDTA and bound radioactivity determined by liquid scintillation counting.

TABLE 1

Binding affinities and receptor selectivity of representative compounds of the invention; reported as $IC_{50}$s.

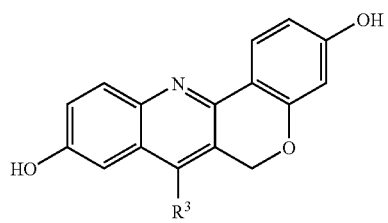

| Cpd | R$^3$ | ERβ(nM) | ERα(nM) | α/β |
|-----|-------|---------|---------|-----|
| 6 | Cl | 3.3 | 88 | 27 |
| 7 | Br | 3.6 | 63 | 18 |
| 8 | CH=CH$_2$ | 31 | 548 | 18 |
| 9 | C≡C—TMS | 225 | 169 | 0.8 |
| 10 | C≡CH | 37 | 131 | 3 |

TABLE 1-continued

Binding affinities and receptor selectivity of representative compounds of the invention; reported as $IC_{50}s$.

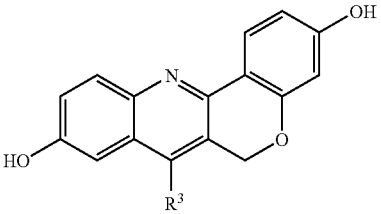

| Cpd | $R^3$ | ERβ(nM) | ERα(nM) | α/β |
|---|---|---|---|---|
| 11 | Et | 5.0 | 66 | 13 |
| 12 | CN | 5.6 | 40 | 7 |
| 13 | 4-Cl—Ph | 160 | 3090 | 19 |
| 14 | 4-ON—Ph | 82 | 1420 | 17 |
| 15 | 4-MeO—Ph | 61 | 357 | 6 |
| 16 | 4-CF₃—Ph | 137 | 6090 | 44 |
| 17 | 3-Cl—Ph | 130 | 505 | 4 |
| 18 | 3-MeO—Ph | 86 | 820 | 10 |
| 19 | 3-CN—Ph | 150 | 1130 | 8 |

The results obtained in this pharmacologic test procedure demonstrate that the compounds of this invention are estrogenic compounds, many with strong preferential affinity for the ERβ receptor. The compounds of this invention range from having high preferential affinity for ERβ over ERα to almost equal affinity for both receptors. Thus, compounds of this invention will span a range of activity based, at least partially, on their receptor affinity selectivity profiles. Additionally, since each novel receptor ligand complex is unique and thus, its interaction with various coregulatory proteins is unique, compounds of this invention will display different modulatory behavior depending on the cellular context they are in. For example, in some cell-types, it is possible for a compound to behave as an estrogen agonist while in other tissues, as an antagonist. Compounds with such activity have sometimes been referred to as SERMs (Selective Estrogen Receptor Modulators). Unlike many estrogens, however, many of the SERMs do not cause increases in uterine wet weight. These compounds are antiestrogenic in the uterus and can completely antagonize the trophic effects of estrogen agonists in uterine tissue. These compounds, however, act as estrogen agonists in the bone, cardiovascular, and central nervous systems. Due to this tissue selective nature of these compounds, they are useful in treating or preventing in a mammal, e.g., a human such as a woman, disease states or syndromes which are caused or associated with an estrogen deficiency (e.g., in certain tissues such as bone or cardiovascular) or an excess of estrogen (e.g., in the uterus or mammary glands).

Even beyond such cell-specific modulation, compounds of this invention also have the potential to behave as agonists on one receptor type while behaving as antagonists on the other. For example, it has been demonstrated that compounds can be an antagonist on ERβ while being an agonist on ERα. (see Meyers, Marvin J. et al., J. Med. Chem. 42(13): 2456-2468 (1999)). Such ERSM (Estrogen Receptor Selective Agonist Antagonist) activity provides for pharmacologically distinct estrogenic activity within this series of compounds.

Other pharmacological test procedures are readily available to determine the activity profile of a representative compound of the invention. The following briefly summarizes several representative test procedures. Pharmacological test procedures for SERMs are also provided in U.S. Pat. Nos. 4,418,068 and 5,998,402, each of which is incorporated by reference in its entirety.

Rat Uterotrophic/Antiuterotrophic Test Procedure

The estrogenic and antiestrogenic properties of the compounds can be determined in an immature rat uterotrophic assay (4 days) (see L. J. Black and R. L. Goode, Life Sciences 26: 1453 (1980)). Immature Sprague-Dawley rats (female, 18 days old) were tested in groups of six. The animals were treated by daily intraperitoneal (ip) injection with 10 μg compound, 100 μg compound, 100 μg compound+1 μg 17β-estradiol (to check antiestrogenicity), and 1 μg 17β-estradiol, with 50% DMSO/50% saline as the injection vehicle. On day 4, the animals were sacrificed by $CO_2$ asphyxiation and their uteri removed and stripped of excess lipid, any fluid removed and the wet weight determined. A small section of one horn was submitted for histology and the remainder used to isolate total RNA to evaluate complement component 3 gene expression.

Six (6)-Week Ovariectomized Rat Test Procedure—Bone and Cardioprotection

Female Sprague Dawley CD rats, ovx or sham ovx, are obtained 1 day after surgery from Taconic (Greenwood, N.Y.) (weight range 240-275 g). They are housed 3 or 4 rats/cage in a room on a 12/12 (light/dark) schedule and provided with food (Purina Mills® 5K96C rat chow) and water ad libitum. Treatment for all studies begin 1 day after the animals' arrival and dosed 7 days per week as indicated for 6 weeks. A group of age matched sham operated rats not receiving any treatment serve as an intact, estrogen replete control group for each study.

All treatments are prepared in 1% Tween 80 in normal saline at defined concentrations so that the treatment volume is 0.1 mL/100 g body weight. 17β estradiol is dissolved in corn oil (20 μg/mL) and delivered subcutaneously, 0.1 mL/rat. All dosages are adjusted at three week intervals according to group mean body weight measurements.

Five weeks after the initiation of treatment and one week prior to the termination of the study, each rat is evaluated for bone mineral density (BMD). The total and trabecular density of the proximal tibia are evaluated in anesthetized rats using an XCT-960M (pQCT ( ); Stratec Medizintechnik, Pforzheim, Germany). The measurements are performed as follows: Fifteen minutes prior to scanning, each rat is anesthetized with an ip injection of 45 mg/kg ketamine, 8.5 mg/kg xylazine, and 1.5 mg/kg acepromazine.

The right hind limb is passed through a polycarbonate tube with a diameter of 25 mm and taped to an acrylic frame with the ankle joint at a 90° angle and the knee joint at 180°. The polycarbonate tube is affixed to a sliding platform that maintains it perpendicular to the aperture of the pQCT. The platform is adjusted so that the distal end of the femur and the proximal end of the tibia would be in the scanning field. A two dimensional scout view is run for a length of 10 mm and a line resolution of 0.2 mm. After the scout view is displayed on the monitor, the proximal end of the tibia is located. The pQCT scan is initiated 3.4 mm distal from this point. The pQCT scan is 1 mm thick, has a voxel (three dimensional pixel) size of 0.140 mm, and consists of 145 projections through the slice.

After the pQCT scan is completed, the image is displayed on the monitor. A region of interest including the tibia but excluding the fibula is outlined. The soft tissue is automatically removed using an iterative algorithm. The density of the remaining bone (total density) is reported in $mg/cm^3$.

The outer 55% of the bone is peeled away in a concentric spiral. The density of the remaining bone (Trabecular density) is reported in mg/cm$^3$. One week after BMD evaluation, the rats are euthanized by carbon dioxide suffocation and blood collected for cholesterol determination. The uteri are removed and the weights taken. Total cholesterol is determined using a Boehringer-Mannheim Hitachi 911 clinical analyzer using the Cholesterol/HP kit. Statistics were compared using one-way analysis of variance (ANOVA) with Dunnet's test.

MCF-7/ERE Antiproliferative Test Procedure

Stock solutions of test compounds (usually 0.1 M) are prepared in DMSO and then diluted 10 to 100-fold with DMSO to make working solutions of 1 or 10 mM. The DMSO stocks are stored at either 4° C. (0.1 M) or −20° C. (<0.1M). MCF-7 cells are passaged twice a week with growth medium [D-MEM/F-12 medium containing 10% (v/v) heat-inactivated fetal bovine serum, 1% (v/v) Penicillin-Streptomycin, and 2 mM glutaMax-1]. The cells are maintained in vented flasks at 37° C. inside a 5% $CO_2$/95% humidified air incubator. One day prior to treatment, the cells are plated with growth medium at 25,000/well into 96 well plates and incubated at 37° C. overnight.

The cells are infected for 2 hours at 37° C. with 50 µl/well of a 1:10 dilution of adenovirus 5-ERE-tk-luciferase in experimental medium [phenol red-free D-MEM/F-12 medium containing 10% (v/v) heat-inactivated charcoal-stripped fetal bovine serum, 1% (v/v) Penicillin-Streptomycin, 2 mM glutaMax-1, 1 mM sodium pyruvate]. The wells are then washed once with 150 µl of experimental medium. Finally, the cells are treated for 24 hours at 37° C. in replicates of 8 wells/treatment with 150 µl/well of vehicle ($\leq$0.1% v/v DMSO) or compound that is diluted$\geq$1000-fold into experimental medium.

Initial screening of test compounds is done at a single dose of 1 µM that is tested alone (agonist mode) or in combination with 0.1 nM 17β-estradiol ($EC_{80}$; antagonist mode). Each 96-well plate also includes a vehicle control group (0.1% v/v DMSO) and an agonist control group (either 0.1 or 1 nM 17β-estradiol). Dose-response experiments are performed in either the agonist and/or antagonist modes on active compounds in log increases from $10^{-14}$ to $10^{-5}$ M. From these dose-response curves, $EC_{50}$ and $IC_{50}$ values, respectively, are generated. The final well in each treatment group contains 5 µl of 3×$10^{-5}$ M ICI-182,780 ($10^{-6}$ M final concentration) as an ER antagonist control.

After treatment, the cells are lysed on a shaker for 15 mins. with 25 µl/well of 1× cell culture lysis reagent (Promega Corporation). The cell lysates (20 µl) are transferred to a 96-well luminometer plate, and luciferase activity is measured in a MicroLumat LB 96 P luminometer (EG & G Berthold) using 100 µl/well of luciferase substrate (Promega Corporation). Prior to the injection of substrate, a 1 second background measurement is made for each well. Following the injection of substrate, luciferase activity is measured for 10 seconds after a 1 second delay. The data are transferred from the luminometer to a Macintosh personal computer and analyzed using the JMP software (SAS Institute); this program subtracts the background reading from the luciferase measurement for each well and then determines the mean and standard deviation of each treatment.

The luciferase data are transformed by logarithms, and the Huber M-estimator is used to down-weight the outlying transformed observations. The JMP software is used to analyze the transformed and weighted data for one-way ANOVA (Dunnett's test). The compound treatments are compared to the vehicle control results in the agonist mode, or the positive agonist control results (0.1 nM 17β-estradiol) in the antagonist mode. For the initial single dose experiment, if the compound treatment results are significantly different from the appropriate control (p<0.05), then the results are reported as the percent relative to the 17β-estradiol control [i.e., ((compound—vehicle control)/(17β-estradiol control—vehicle control))×100]. The JMP software is also used to determine the $EC_{50}$ and/or IC $C_{50}$ values from the non-linear dose-response curves.

Inhibition of LDL Oxidation—Antioxidant Activity

Porcine aortas are obtained from an abattoir, washed, transported in chilled phosphate buffered saline (PBS), and aortic endothelial cells are harvested. To harvest the cells, the intercostal vessels of the aorta are tied off and one end of the aorta clamped. Fresh, sterile filtered, 0.2% collagenase (Sigma Type I) is placed in the vessel and the other end of the vessel then clamped to form a closed system. The aorta is incubated at 37° C. for 15-20 mins., after which the collagenase solution is collected and centrifuged for 5 mins. at 2000×g. Each pellet is suspended in 7 mL of endothelial cell culture medium consisting of phenol red free DMEM/Ham's F12 media supplemented with charcoal stripped fetal bovine serum (FBS; 5%), NuSerum® (5%), L-glutamine (4 mM), penicillin-streptomycin (1000 U/ml, 100 µg/ml) and gentimicin (75 µg/ml), seeded in a 100 mm petri dish and incubated at 37° C. in 5% $CO_2$. After 20 minutes, the cells are rinsed with PBS and fresh medium added, and again, at 24 hours. The cells are confluent after approximately 1 week. The endothelial cells are routinely fed twice a week and, when confluent, trypsinized and seeded at a 1:7 ratio. Cell mediated oxidation of 12.5 µg/mL LDL is allowed to proceed in the presence of the compound to be evaluated (5 µM) for 4 hours at 37° C. Results are expressed as the percent inhibition of the oxidative process as measured by the TBARS (thiobarbituric acid reactive substances) method for analysis of free aldehydes (Yagi K., *Biochem Med* 15:212-216 (1976)).

D12 Hypothalmic Cell Test Procedure

D12 rat hypothalmic cells are subcloned from the RCF17 parental cell line and stored frozen. They are routinely grown in DMEM:F12 (1:1), glutaMAX-1 (2 mM), penicillin (100 U/ml)-streptomycin (100 mg/ml), plus 10% FBS. The cells are plated in phenol red-free medium (DMEM:F12, glutaMAX, penicillin-streptomycin) containing 2-10% charcoal stripped FBS at a subconfluent density (1-4×$10^6$ cells/150 mm dish). The cells are refed 24 hours later with medium containing 2% stripped serum. To test for agonist activity, cells are treated with 10 nM 17β-estradiol or various doses of test compound (1 mM or a range from 1 pM to 1 mM). To test for antagonist activity, the cells are treated with 0.1 nM 17β-estradiol in the absence or presence of varying doses (100 pM to 1 mM) of test compound. Control dishes are also treated with DMSO as a negative control. Forty-eight hours after hormone addition, the cells are lysed and a binding test procedure performed.

For each binding test procedure 100-150 mg protein is incubated with 10 nM $^3$H-R5020+100-fold excess R5020 in a 150 mL volume. Triplicate reactions (three with R5020, three without R5020) are prepared in a 96-well plate. The protein extract is added first followed by H-R5020 or H-R5020+100× unlabeled R5020. The reaction is performed for 1-2 hour(s) at room temperature. The reaction is stopped by the addition of 100 mL cold 5% charcoal (Norit SX-4), 0.5% dextran 69K (Pharmacia) in TE, pH 7.4. After 5 mins. at room temperature, the bound and unbound ligand are separated by centrifugation (5 mins., 1000 RCF, 4° C.). The supernatant solution (~150 ml) is removed and transferred to a scintillation vial. Following the addition of scintillation fluid (Beckman Ready Protein+), the samples are counted for 1 min. in a scintillation counter.

Progesterone Receptor in the CNS Preoptic Area

Sixty (60) days old female Sprague-Dawley rats are ovariectomized. The animals are housed in an animal care facility with a 12-hour light, 12-hour dark photoperiod and free access to tap water and rodent chow.

Ovariectomized animals are randomly divided into groups that are injected with vehicle (50% DMSO, 40% PBS, 10% ethanol vehicle), 17β-estradiol (200 ng/kg) or the compound to be tested. Additional animals are injected with the test compound 1 hour prior to injection of 17β-estradiol to evaluate the antagonistic properties of this compound. Six hours after subcutaneous (sc) injection, the animals are euthanized with a lethal dose of $CO_2$ and their brains collected and frozen.

Tissue collected from the animals is cut on a cryostat at −16° C. and collected on Silane-coated microscope slides. The section-mounted slides are then dried on a slide warmer maintained at 42° C. and stored in desiccated slide boxes at −80° C. Prior to processing, the desiccated slide boxes are slowly warmed to room temperature (−20° C. for 12-16 hours; 4° C. for 2 hours; room temperature for 1 hour) to eliminate condensation formation on slides and thus, minimize tissue and RNA degradation. The dry slides are loaded into metal racks, post-fixed in 4% paraformaldehyde (pH 9.0) for 5 mins. and processed, as previously described.

A plasmid containing a 815 bp fragment of the rat PR cDNA 9 (ligand binding domain) is linearized and used to generate a S 35-UTP labeled probe that is complimentary to a portion of the rat PR mRNA. Processed section-mounted slides are hybridized with 200 mL of hybridization mix containing the riboprobe ($4-6\times10^6$ DPM/slide) and 50% formamide, and incubated overnight in a 55° C. humidified chamber. In the morning, the slides are placed in metal racks that are immersed in 2×SSC (0.15M NaCl, 0.015M sodium citrate; pH 7.0)/10 mM DTT. The racks are all transferred to a large container and washed in 2×SSC/10 mM DTT for 15 mins. at room temperature with gentle agitation. Slides are then washed in RNase buffer at 37° C. for 30 mins., treated with RNase A (2 mg/ml) for 30 mins. at 37° C., and washed for 15 mins. in room temperature 1×SSC. Subsequently, the slides are washed (2×30 mins.) in 65° C. in 0.1×SSC to remove nonspecific label, rinsed in room temperature 0.1× SSC for 15 mins. and dehydrated with a graded series of alcohol: ammonium acetate (70%, 95%, and 100%). Air dried slides are opposed to x-ray film for 3 days and then photographically processed. The slides from all animals are hybridized, washed, exposed and photographically processed together to eliminate differences due to interassay variation in conditions.

Rat Hot Flush—CNS Effects

Ovariectomized-female, 60 days-old, Sprague-Dawley rats are obtained following surgery. The surgeries are done a minimum of 8 days prior to the first treatment. The animals are housed individually under a 12/12 hours light/dark cycle and given standard rat chow and water ad libitum.

Two control groups are included in every study. Doses are prepared based on mg/kg mean group body weight in either 10% DMSO in sesame oil (sc studies) or in 1.0% Tween 80 in saline ((po) studies). Animals are administered test compounds at doses ranging from 0.01 to 10 mg/kg mean group body weight. Vehicle and ethinyl estradiol (EE) controls (0.1 mg/kg, sc or 0.3 mg/kg, po) control groups are included in each test. When the compounds are tested for their antagonist activity, EE is coadministered at 0.1 or 0.3 mg/kg for sc or po studies, respectively. The test compounds are administered up to the day that tail skin temperature is measured.

After the acclimation period of four days, the animals are treated once daily with the compound(s) of interest. There are 10 animals/treatment group. Administration of the compound is either by sc injection of 0.1 ml in the nape of the neck or po in a volume of 0.5 ml. On the 3rd day of treatment, a morphine pellet (75 mg morphine sulfate) is implanted subcutaneously. On the 5th day of treatment, one or two additional morphine pellets are implanted. On the eighth day, approximately half of the animals are injected with Ketamine (80 mg/kg, intramuscularly) and a thermocouple, connected to a MacLab Data Acquisition System (API Instruments, Milford, Mass.) is taped on the tail approximately one inch from the root of the tail. This system allowed the continuous measurement of tail skin temperature. Baseline temperature is measured for 15 mins., then naloxone (1.0 mg/kg) is given sc (0.2 mL) to block the effect of morphine, and tail skin temperature is measured for one hour thereafter. On the ninth day, remaining animals are set up and analyzed similarly.

Vasomotor Function in Isolated Rat Aortic Rings

Sprague-Dawley rats (240-260 grams) are divided into 4 groups:
1. Normal non-ovariectomized (intact)
2. Ovariectomized (ovex) vehicle treated
3. Ovariectomized 17-β estradiol treated (1 mg/kg/day)
4. Ovariectomized animals treated with test compound (i.e., 1 mg/kg/day).

The animals are ovariectomized approximately 3 weeks prior to treatment. Each animal receives 1 mg/kg/day of either 17-β estradiol sulfate or test compound suspended in distilled, deionized water with 1% Tween-80 by gastric gavage. Vehicle treated animals received an appropriate volume of the vehicle used in the drug treated groups.

Animals are euthanized by $CO_2$ inhalation and exsanguination. Their thoracic aortas are rapidly removed and placed in 37° C. physiological solution with the following composition (mM): NaCl (54.7), KCl (5.0), $NaHCO_3$ (25.0), $MgCl_2$-$2H_2O$ (2.5), D-glucose (11.8) and $CaCl_2$ (0.2) gassed with $CO_2$—$O_2$, 95%/5% for a final pH of 7.4. The advantitia is removed from the outer surface and the vessel is cut into 2-3 mm wide rings. The rings are suspended in at 10 mL tissue bath with one end attached to the bottom of the bath and the other to a force transducer. A resting tension of 1 gram is placed on the rings. Rings are equilibrated for 1 hour, while signals are acquired and analyzed.

After equilibration, the rings are exposed to increasing concentrations of phenylephrine ($10^{-8}$ to $10^{-4}$ M) and the tension recorded. Baths are then rinsed 3 times with fresh buffer. After washout, 200 mM L-NAME is added to the tissue bath and equilibrated for 30 minutes. The phenylephrine concentration response curve is then repeated.

Eight Arm Radial Arm Maze—Cognition Enhancement

Male, Sprague-Dawley, CD rats (Charles River, Kingston, N.Y.) weighing 200-250 g on arrival are used. For one week, the rats are housed, six per cage, with standard laboratory chow and water available ad libitum. Housing is in a colony room maintained at 22° C. with a 12/12 hours light/dark cycle with lights on at 6:00 AM. Following habituation to the facility, the animals are individually housed and maintained at 85% of free-feeding weight. Once stable weights are attained, the rats are acclimated to the 8-arm radial maze.

The structure of the maze is an adaptation from that of Peele and Baron (*Pharmacology, Biochemistry, and Behavior* 29:143-150 (1988)). The maze is elevated to a height of 75.5 cm and composed of a circular area surrounded by 8 arms radiating away from the center, equidistant from one another. Each arm is 58 cm long×13 cm high. A clear plexiglass cylinder is lowered to enclose the animal in the center portion of the maze prior to the start of each session. Each arm of the maze is equipped with 3 sets of photocells interfaced to a data acquisition unit, which in turn is interfaced to a computer. The photocells are used to track the movement of the rat in the maze. Pellet feeders located above food cups at the end of each arm, dispensed two 45 mg chocolate pellets when the outer photocell of the arm is activated for the first time in a given session. The maze is located in a testing room with black and white geometric posters on each wall to serve as visual cues. During all training and testing procedures, white noise is audible (~70 db).

The training procedure consists of five phases, each with daily sessions lasting 5 or 10 minutes. A 10 second delay is imposed between the time the rat is placed in the center portion of the maze and when the cylinder is raised to begin the session. During Phase 1, food-restricted pairs of rats are placed on the maze for 10 minutes with 45 mg chocolate food pellets scattered throughout the 8 arms of the maze. During Phase II, each rat is placed individually on the maze for a 10 minute period, with pellets scattered from the middle photocell to the food cup of each arm. During Phase III, each rat is placed on the maze for a 10 minute period, with food pellets located only in and around the food cups in each arm. In Phase IV, each rat is allowed 10 minutes to collect two pellets from each arm. Re-entry into an arm is considered an error. Rats are trained daily in this manner until they achieved criterion performance with less than or equal to 2 total errors on three consecutive days of training. Total habituation and training time is approximately 3 weeks.

Test compound is prepared in phosphate buffered saline and administered in a volume of 1 ml/kg. Scopolamine HBr (0.3 mg/kg sc) served as the impairing agent, producing an increase in error rate (loss of memory). Test compound is given intraperitoneally, simultaneously with scopolamine, 30 minutes prior to the first maze exposure on any given test day.

To assess the test compound, an 8×8 balanced Latin square for repeated measures is designed, in order to achieve a high experimental efficiency with the least amount of animals. Eight experimental sessions, two per week, are conducted with the 8 treatments (vehicle, scopolamine, 3 doses of test compound in combination with scopolamine) randomized within each session. Each treatment followed every other treatment the same number of times. Therefore, the residual effect of every treatment could be estimated and removed from the direct treatment effect. Following ANOVA, multiple comparisons are performed using Dunnett's two-sided test on adjusted means.

Animals that do not make 4 correct choices within 5 minutes during the first exposure, or that have not made a total of 8 choices by the end of the second exposure, are considered to have "timed-out" for that session. Any animal that "timed-out" following administration of more than one dose of the test compound is excluded from the analysis.

Neuroprotection

Inhibition of Time-Dependent Death of Cells in Primary Cortical Neuron Cultures

Primary cortical neurons were produced from rat brains that were 0-1 day old using a variation of methods described by Monyer et al., *Brain Research* 483:347-354 (1989). Dispersed brain tissue was grown in DMEM/10% PDHS (pregnant donor horse serum) for three days and then treated with cytosine arabinoside (ARC) for two days to remove contaminating glial cells. On day 5, the ARC media was removed and replaced with DMEM/10% PDHS. The neuronal cells were cultured for a further 4-7 days before use.

Control primary neuronal cultures show progressive cell death between days 12 and 18 in culture. Twelve cultures were evaluated on days 12 and 16 for levels of the enzyme lactate dehydrogenase (LD) after adding test compound to 6 cultures maintained in DMEM and 10% PDHS on day 9 and maintaining the remaining cultures as controls. LD was assayed using a variation of the method by Wroblewski et al., *Proc. Soc. Exp. Biol. Med.* 90:210-213 (1955). LD is a cytosolic enzyme that is commonly used in both clinical and basic research to determine tissue viability. An increase in media LD is directly related to cell death.

Neuroprotection Against Cytotoxicity Induced by Hypoglycemia

C6 glioma cells obtained from American Tissue Culture Center (ATCC) were plated in RPMI media with FBS at a concentration of $1 \times 10^6$ cells/mL in FALCON® 25 $cm^2$ tissue culture flasks. Four hours prior to the onset of hypoglycemia, the maintenance media was discarded, monolayers were washed twice in the appropriate media and then incubated for four hours at 37° C. in either serum free or serum free plus test compound. Kreb's Ringer Phosphate buffer was used to wash the monolayers twice before the addition of appropriate glucose treatment. RPMI medium contains 2 mg glucose/mL; flasks were divided into groups of 6 with each receiving 100% glucose (2 mg/ml), 80% glucose (1.6 mg/ml), 60% glucose (1.2 mg/ml) or 0% glucose (buffer) or supplemented with test compound. All flasks were incubated for 20 hours and then evaluated for total, live, and dead cell number utilizing trypan blue.

Neuroprotection Against Excitotoxic Amino Acids

Five culture dishes containing SK—N—SH neuroblastoma cells were treated with test compound and 5 culture dishes were treated with RPMI media. Four hours later, all cell were treated with NMDA (500 µM) for 5 minutes. Total live cells and dead cells were then determined.

Neuroprotection Against Oxygen-Glucose Deprivation—Analysis of Pyknotic Nuclei to Measure Apoptosis Cortical neurons are prepared from E18 rat fetus and plated in 8-well chamber slides pre-coated with poly-D-lysine (10 ng/ml) and serum at a density of 100,000 cells/well. Cells are plated in high glucose DMEM containing 10% FCS and kept in the incubator at 37° C. with 10% $CO_2$/90% air. On the next day, serum is removed by replacing culture media with high glucose DMEM containing B27 supplement, and cells are kept in the incubator without further media change until the day of experiment. On day 6, slides are divided into two groups: a control group and a OGD group. Cells in the control group receive DMEM with glucose and custom B27 (without antioxidants). Cells in the OGD group receive no-glucose DMEM with custom B27, which has been degassed under vacuum for 15 mins. Cells are flushed with 90% $N_2$/10% $CO_2$ for 10 mins. in an airtight chamber and incubated at 37° C. for 6 hours. After 6 hours, both control and OGD cells are subject to replacement of media containing either vehicle (DMSO) or test compound in glucose-containing DMEM with custom B27. Cells are returned to a normoxic incubator at 37° C. After 24 hours, cells are fixed in 4% PFA for 10 mins. at 4° C. and stained with Topro (fluorescent nuclear binding dye). Apoptosis is assessed using a laser scanning cytometer by measuring pyknotic nuclei.

Measurement of LDH Release as an Indication of Cell Death

Cortical neurons are prepared from E18 rat fetus and plated in 48-well culture plates pre-coated with poly-D-lysine (10 ng/ml) and serum at a density of 150,000 cells/well. Cells are plated in high glucose DMEM containing 10% FCS and kept in the incubator at 37° C. with 10% $CO_2$/90% air. On the next day, serum is removed by replacing culture media with high glucose DMEM containing B27 supplement. On day 6, cells are divided into two groups: a control group and a OGD group. Cells in the control group receive DMEM with glucose and custom B27 (without antioxidants). Cells in the OGD group receive no-glucose DMEM with custom B27, which has been degassed under vacuum for 15 mins. Cells are flushed with 90% $N_2$/10% $CO_2$ for 10 mins. in an airtight chamber and incubated at 37° C. for 6 hours. After 6 hours, both control and OGD cells are subject to replacement of media containing either vehicle (DMSO) or test compound in glucose-containing DMEM with custom B27. Cells are returned to a normoxic incubator at 37° C. After 24 hours, cell death is assessed by measuring cellular release of LDH (lactate dehydrogenase) into the culture medium. For the LDH assay, an aliquot of 50 µl culture medium is transferred into the 96-well plate. After the addition of 140 µl 0.1M potassium phosphate buffer (pH 7.5) and 100 µl 0.2 mg/ml NADH, the plate is allowed to sit in the dark at room temperature for 20 mins. The reaction is initiated by the addition of 10 µl of sodium pyruvate. The plate is read immediately at 340 nM in a Thermomax plate reader (Molecular Devices). The absorbance, an index of NADH concentration, is recorded every 6 seconds for 5 minutes and the slope indicating the rate of NADH disappearance is used to calculate LDH activity:

$$LDH\ Activity(U/ml) = (\Delta A/min)(TCF)(20)(0.0833)/(0.78)$$

where:
0.0833=proportionality constant and
0.78=instrument light path length (cm).

HLA Rat Test Procedure—Crohn's Disease and Inflammatory Bowel Disorders

Male HLA-B27 rats are obtained from Taconic and provided unrestricted access to a food (Purina Mills® LabDiet® 5001) and water. At the start of the study, rats are 22-26 weeks old.

Rats are dosed subcutaneously once per day for seven days with one of the formulations listed below. There are five rats in each group and the last dose is administered two hours before euthanasia.

Vehicle (50% DMSO/50% Dulbecco's PBS);
17α-ethinyl-17β-estradiol (10 µg/kg); or
test compound.

Stool quality is observed daily and graded according to the following scale: Diarrhea=3; soft stool=2; normal stool=1. At the end of the test procedure, serum is collected and stored at −70° C. A section of colon is prepared for histological analysis and an additional segment is analyzed for myeloperoxidase activity.

The following method is used to measure myeloperoxidase activity. Colon tissue is harvested and flash frozen in liquid nitrogen. A representative sample of the entire colon is used to ensure consistency between samples. The tissue is stored at −80° C. until use. Next, the tissue is weighed (approximately 500 mg) and homogenized in 1:15 w/v of 5 mM $H_2\ KPO_4$ (pH 6) washing buffer. The tissue is spun down at 20,000×g in a Sorvall RC 5B centrifuge for 45 minutes at 2-8° C. Supernatant is then discarded. Tissue is resuspended and homogenized in 2.5 mL (1:5 w/v) of 50 mM $H_2\ KPO_4$ with 10 mM EDTA and 0.5% Hex Ammonium Bromide to help solubilize the intracellular MPO. Tissue is frozen in liquid nitrogen, thawed in a 37° C.-water bath and sonicated for 15 seconds to ensure membrane lysis. This procedure is repeated 3 times. Samples are then kept on ice for 20 minutes and centrifuged at 12,000×g for 15 minutes at 2-8° C. The supernatant is analyzed following these steps.

The test mixture is prepared by adding 2.9 mL of 50 mM $H_2\ KPO_4$ with 0.167 O-Dianisidine/ml with 0.0005% $H_2O_2$ into a reaction tube. When hydrogen peroxide is degraded, O-Dianisidine is oxidized and absorbs at 460 nm in a concentration dependent manner. The mixture is heated to 25° C. One hundred (100) µL of the tissue supernatant is added to the reaction tube and incubated for one minute at 25° C., then 1 ml is transferred to a disposable plastic cuvette. Optical density (OD) is measured every 2 minutes of reaction time at 460 nm against a blank containing 2.9 mL of reaction mixture and 100 µL of the 0.5% ammonium bromide solution.

Enzyme activity units are quantified by comparison of absorbance at 460 nm to a standard curve prepared with purified human MPO 31.1 units/vial. The MPO is reconstituted and serially diluted using 50 mM $H_2\ KPO_4$ with 10 mM EDTA and 0.5% Hex Ammonium Bromide to four known concentrations. Sample absorbancies are compared against this curve to determine activity.

Histological analysis is performed as follows. Colonic tissue is immersed in 10% neutral buffered formalin. Each specimen of colon is separated into four samples for evaluation. The formalin-fixed tissues are processed in a vacuum infiltration processor for paraffin embedding. The samples are sectioned at 5 µm and then stained with hematoxylin and eosin (H&E) for blinded histologic evaluations using a scale modified after Boughton-Smith. After the scores are completed the samples are unblinded, and data are tabulated and analyzed by ANOVA linear modeling with multiple mean comparisons.

Based on the results obtained in the standard pharmacological tests procedures, as described herein, the compounds of this invention are estrogen receptor modulators useful in the treatment or inhibition of conditions, disorders, or disease states that are at least partially mediated by an estrogen deficiency or excess, or which may be treated or inhibited through the use of an estrogenic agent.

It is intended that each of the patents, applications, and printed publications, including books, mentioned in this patent document be incorporated herein by reference in their entirety. As those skilled in the art will appreciate, numerous changes and modifications may be made to the preferred embodiments of the invention without departing from the spirit of the invention. It is intended that all such variations fall within the scope of the invention.

The invention claimed is:

1. A compound of formula I having structure:

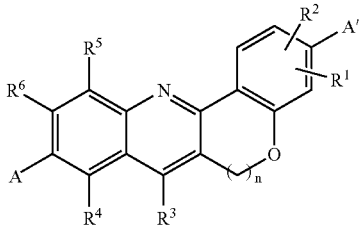

wherein:
A and A' are each independently OH, H or OR;
each R is independently selected from the group consisting of $C_1$-$C_6$ alkyl, alkenyl, benzyl, acyl, aroyl, —C(=O)—OR', sulfonyl and phosphorl, wherein each R' is independently selected from $C_1$-$C_6$ alkyl, alkenyl, $C_2$-$C_7$ alkynyl, or $C_3$-$C_{10}$ cycloalkyl, each of which which are optionally substituted by 1 to 3 substituents selected from $C_1$-$C_6$ alkyl or halogen;
$R^1$ and $R^2$ are independently selected from the group consisting of H, halogen, $C_1$-$C_6$ alkyl, $C_1$-$C_6$ perhaloalkyl, $CF_3$, $C_2$-$C_7$ alkenyl and $C_1$-$C_6$ alkoxy;
$R^3$, $R^4$, and $R^5$ are each independently selected from the group consisting of H, halogen, $CF_3$, $C_1$-$C_6$ perhaloalkyl, $C_1$-$C_6$ alkyl, $C_2$-$C_7$ alkenyl, $C_2$-$C_7$ alkynyl, $C_3$-$C_7$ cycloalkyl, CN, —CHO, acyl, aryl and heteroary;
$R^6$ is selected from the group consisting of H, $CF_3$, $C_1$-$C_6$ perhaloalkyl, $C_1$-$C_6$ alkyl, $C_2$-$C_7$ alkenyl, $C_2$-$C_7$ alkynyl, $C_3$-$C_7$ cycloalkyl, CN, —CHO, acyl, acyl and heteroaryl;
wherein the alkyl or alkenyl moieties of $R^3$, $R^4$, $R^5$ and $R^6$ can each be optionally substituted with up to three substituents independently selected from halogen, OH, CN, trifluoroalkyl, trifluoroalkoxy, $NO_2$ or phenyl, wherein said phenyl is optionally substituted with up to three independently selected $R^{10}$ groups;
wherein the alkynyl moiety of $R^3$, $R^4$, $R^5$ and $R^6$ can each be optionally substituted with up to three substituents selected from halogen, —CN, —CHO, acyl, trifluoroalkyl, trialkylsilyl or phenyl, wherein said phenyl is optionally substituted with up to three independently selected $R^{10}$ groups;
wherein the aryl or heteroaryl moiety of $R^3$, $R^4$, $R^5$ and $R^6$ can each be optionally substituted with up to three substituents selected from halogen, —CN, alkyl, alkoxy, perfluoroalkyl or perfluoroalkoxy;
each $R^{10}$ is independently selected from the group consisting of halogen, $C_1$-$C_6$ alkyl, $C_2$-$C_7$ alkenyl, —OH, $C_1$-$C_6$ alkoxy, —CN, —CHO, —$NO_2$, amino, $C_1$-$C_6$ alkylamino, di-($C_1$-$C_6$) alkylamino, thiol, and $C_1$-$C_6$ alkylthio; and
n is 0, 1, 2, or 3;
provided that:
at least one of A and A' is not H;
if n is 0, then $R_3$ is not halogen; and
at least one of $R^3$, $R^4$ and $R^5$ is halogen, $C_1$-$C_6$ alkyl, $C_2$-$C_7$ alkenyl, $C_2$-$C_7$ alkynyl, $C_3$-$C_7$ cycloalkyl, —CN, —CHO, acyl, aryl or heteroaryl; or an N-oxide thereof or a pharmaceutically acceptable salt thereof.

2. The compound of claim 1 wherein A and A' are each OH.

3. The compound of claim 1 wherein one of A and A' is OH, and the other of A and A' is OR.

4. The compound of claim 1 wherein one of A and A' is OH, and the other of A and A' is O—$C_1$-$C_6$ alkyl.

5. The compound of claim 1 wherein A and A' are each OR.

6. The compound of claim 5 wherein A and A' are each —O—$C_1$-$C_6$ alkyl.

7. The compound of claim 1 wherein one of A and A' is H, and the other of A and A' is OH or OR.

8. The compound of claim 1 wherein one of A and A' is H, and the other of A and A' is OH or O—$C_1$-$C_6$ alkyl.

9. The compound of claim 1 wherein $R^3$ and $R^5$ are each, independently, H, halogen, $C_1$-$C_6$ alkyl, $C_2$-$C_7$ alkenyl, $C_2$-$C_7$ alkynyl, —CN, —CHO, acyl or optionally substituted phenyl, as previously defined.

10. The compound of claim 9 wherein $R^3$ is other than H.

11. The compound of claim 1 wherein $R^3$ is halogen, $C_1$-$C_6$ alkyl, $C_2$-$C_7$ alkenyl, $C_2$-$C_7$ alkynyl, —CN, —CHO, or phenyl optionally substituted with up to three groups selected from halogen, $C_1$-$C_6$ alkoxy, perfluoroalkyl and CN; and $R^5$ is H, halogen, $C_1$-$C_6$ alkyl, $C_2$-$C_7$ alkenyl, $C_2$-$C_7$ alkynyl, —CN, —CHO, or phenyl optionally substituted with up to three groups selected from halogen, $C_1$-$C_6$ alkoxy, perfluoroalkyl and CN.

12. The compound of claim 11 wherein said phenyl of said $R^3$ is optionally substituted with up to three substituents selected from F, Cl, Br, CN, $OCH_3$ and $CF_3$.

13. The compound of claim 1 wherein $R^3$ is halogen, $C_2$-$C_7$ alkynyl or —CN.

14. The compound of claim 1 wherein $R^3$ and $R^5$ are each independently halogen, $C_2$-$C_7$ alkynyl or —CN.

15. The compound of claim 1 wherein one of $R^1$ and $R^2$ is halogen.

16. The compound of claim 1 wherein one of $R^1$ and $R^2$ is fluorine.

17. The compound of claim 1 wherein one of $R^1$ and $R^2$ is halogen, and the other of $R^1$ and $R^2$ is H.

18. The compound of claim 1 wherein one of $R^1$ and $R^2$ is fluorine, and the other of $R^1$ and $R^2$ is H.

19. The compound of claim 1 wherein $R^1$ and $R^2$ are each independently halogen.

20. The compound of claim 1 wherein $R^1$ and $R^2$ are each H.

21. The compound of claim 1 wherein $R^1$ and $R^2$ are each fluorine.

22. The compound of claim 1 wherein $R^4$ is H, halogen or —CN.

23. The compound of claim 1 wherein $R^4$ is H.

24. The compound of any of claims 1-8 wherein:
$R^3$ is halogen, $C_1$-$C_6$ alkyl, $C_2$-$C_7$ alkenyl, $C_2$-$C_7$ alkynyl, —CN, —CHO, or phenyl optionally substituted with up to three groups selected from halogen, $C_1$-$C_6$ alkoxy, perfluoroalkyl and CN;
$R^5$ is H, halogen, $C_1$-$C_6$ alkyl, $C_2$-$C_7$ alkenyl, $C_2$-$C_7$ alkynyl, —CN, —CHO, or phenyl optionally substituted with up to three groups selected from halogen, $C_1$-$C_6$ alkoxy, perfluoroalkyl and CN;
one of $R^1$ and $R^2$ is halogen; and $R^4$ is H, halogen or —CN.

25. The compound of claim 2 wherein $R^3$ is halogen, and $R^1$, $R^2$, $R^4$, $R^5$ and $R^6$ are hydrogen.

26. The compound of claim 2 wherein $R^3$ is $C_2$-$C_7$ alkenyl, and $R^1$, $R^2$, $R^4$, $R^5$ and $R^6$ are hydrogen.

27. The compound of claim 2 wherein $R^3$ is CN, and $R^1$, $R^2$, $R^4$, $R^5$ and $R^6$ are hydrogen.

28. The compound of claim 2 wherein $R^3$ is $C_2$-$C_7$ alkynyl, and $R^1$, $R^2$, $R^4$, $R^5$ and $R^6$ are hydrogen.

29. The compound of claim 6 wherein $R^3$ is $C_1$-$C_6$ alkyl, and $R^1$, $R^2$, $R^4$, $R^5$ and $R^6$ are hydrogen.

30. The compound of claim 6 wherein $R^3$ is optionally substituted phenyl, and $R^1$, $R^2$, $R^4$, $R^5$ and $R^6$ are hydrogen.

31. The compound of claim 30 wherein said substituents of said phenyl are selected from the group consisting of halogen, $C_1$-$C_6$ alkoxy, perfluoroalkyl and CN.

32. The compound of any of claims 1-23 and 25 or 27-31 wherein n is 1.

33. The compound of claim 24 wherein n is 1.

34. A compound which is:
a) 3,9-Dimethoxy-6H-chromeno[4,3-b]quinolin-7-ol;
b) 7-Chloro-3,9-dimethoxy-6H-chromeno[4,3-b]quinoline;
c) 7-Bromo-3,9-dimethoxy-6H-chromeno[4,3-b]quinoline;
d) 7-Chloro-3,9-dihydroxy-6H-chromeno[4,3-b]quinoline;
e) 7-Bromo-3,9-dihydroxy-6H-chromeno[4,3-b]quinoline;
f) 3,9-Dihydroxy-7-vinyl-6H-chromeno[4,3-b]quinoline;
g) 3,9-Dihydroxy-7-[(trimethylsilyl)ethynyl]-6H-chromeno[4,3-b]quinoline;
h) 3,9-Dihydroxy-7-ethynyl-6H-chromeno[4,3-b]quinoline;
i) 3,9-Dihydroxy-7-ethyl-6H-chromeno[4,3-b]quinoline;
j) 7-Cyano-3,9-dihydroxy-6H-chromeno[4,3-b]quinoline;
k) 7-(4-Chlorophenyl)-3,9-dihydroxy-6H-chromeno[4,3-b]quinoline;
l) 7-(4-Cyanophenyl)-3,9-dihydroxy-6H-chromeno[4,3-b]quinoline;
m) 3,9-Dihydroxy-7-(4-methoxyphenyl)-6H-chromeno[4,3-b]quinoline;
n) 3,9-Dihydroxy-7-[4-(trifluoromethyl)phenyl]-6H-chromeno[4,3-b]quinoline;
o) 7-(3-Chlorophenyl)-3,9-dihydroxy-6H-chromeno[4,3-b]quinoline;
p) 3,9-Dihydroxy-7-(3-methoxyphenyl)-6H-chromeno[4,3-b]quinoline;
q) 7-(3-Cyanophenyl)-3,9-dihydroxy-6H-chromeno[4,3-b]quinoline;
or pharmaceutically acceptable salts, chelates, complexes or prodrugs thereof.

35. A composition comprising a compound according to claim 34.

36. A composition comprising a compound according to claim 1.

37. A method for the preparation of a compound of Formula IV:

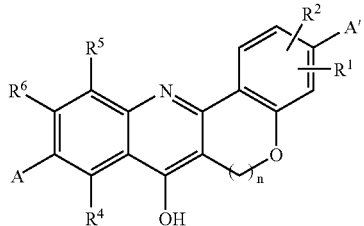

IV wherein:

A and A' are each independently OH, H or OR;

each R is independently selected from the group consisting of $C_1$-$C_6$ alkyl, alkenyl, benzyl, acyl, aroyl, —C(=O)—CR', sulfonyl and phosphoryl, wherein each R' is independently selected from $C_1$-$C_6$ alkyl, $C_2$-$C_7$ alkenyl, $C_2$-$C_7$ alkynyl, or $C_3$-$C_{10}$ cycloalkyl, each of which are optionally substituted by 1 to 3 substituents selected from $C_1$-$C_6$ alkyl or halogen;

$R^1$ and $R^2$ are independently selected from the group consisting of H, halogen, $C_1$-$C_6$ alkyl, $C_1$-$C_6$ perhaloalkyl, $CF_3$, $C_2$-$C_7$ alkenyl and $C_1$-$C_6$ alkoxy;

$R^4$, $R^5$ and $R^6$ are each independently selected from the group consisting of H, halogen, $CF_3$, $C_1$-$C_6$ perhaloalkyl, $C_1$-$C_6$ alkyl, $C_2$-$C_7$ alkenyl, $C_2$-$C_7$ alkynyl, $C_3$-$C_7$ cycloalkyl, CN, —CHO, acyl, aryl and heteroaryl;

wherein the alkyl or alkenyl moieties of $R^4$, $R^5$ and $R^6$ can each be optionally substituted with up to three substituents independently selected from halogen, OH, CN, trifluoroalkyl, trifluoroalkoxy $NO_2$ or phenyl, wherein said phenyl is optionally substituted with up to three independently selected $R^{10}$ groups;

wherein the alkynyl moiety of $R^4$, $R^5$ and $R^6$ can each be optionally substituted with up to three substituents selected from halogen, —ON, —CHO, acyl, trifluoroalkyl, trialkylsilyl or phenyl, wherein said phenyl is optionally substituted with up to three independently selected $R^{10}$ groups;

wherein the aryl or heteroaryl moiety of $R^4$, $R^5$ and $R^6$ can each be optionally substituted with up to three substituents selected from halogen, —ON, alkyl, alkoxy, perfluoroalkyl or perfluoroalkoxy;

each $R^{10}$ is independently selected from the group consisting of halogen, $C_1$-$C_6$ alkyl, $C_2$-$C_7$ alkenyl, —OH, $C_1$-$C_6$ alkoxy, —CN, —CHO, —$NO_2$, amino, $C_1$-$C_6$ alkylamino, di-($C_1$-$C_6$)aikylamino, thiol, and $C_1$-$C_6$ alkylthio; and n is 0,1,2, or 3;

provided that:

at least one of A and A' is not H; and at least one of $R^4$ and $R^5$ is halogen, $C_1$-$C_6$ alkyl, $C_2$-$C_7$ alkenyl, $C_2$-$C_7$ alkynyl, $C_3$-$C_7$ cycloalkyl, $C_1$-$C_6$ alkoxy, —CN, —CHO, acyl, phenyl, aryl or heteroaryl; or an N-oxide thereof or a pharmaceutically acceptable salt thereof; comprising the steps of:

r) providing a compound of Formula II:

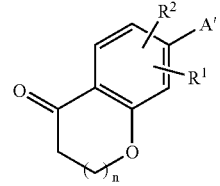

II and;
s) reacting the compound of Formula II with a compound of Formula III:

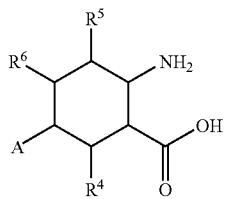

to produce the compound of Formula IV.

38. The method of claim 37 further comprising the step of contacting the compound of Formula IV with a modifying reagent to form a compound of Formula I:

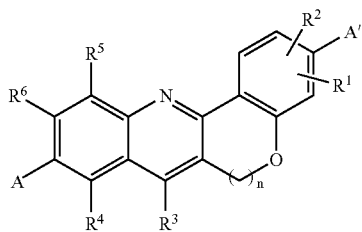

wherein:
$R^3$ is selected from the group consisting of H, halogen, $CF_3$, $C_1$-$C_6$ perhaloalkyl, $C_1$-$C_6$ alkyl, $C_2$-$C_7$ alkenyl, $C_2$-$C_7$ alkynyl, $C_3$-$C_7$ cycloalkyl, $C_1$-$C_6$ alkoxy, CN, —CHO, acyl, aryl and heteroaryl;

wherein the alkyl or alkenyl moieties of $R^3$ are optionally substituted with up to three substituents independently selected from halogen, OH, CN, trifluoroalkyl, trifluoroalkoxy, $NO_2$ and phenyl, wherein said phenyl is optionally substituted with up to three independently selected $R^{10}$ groups;

wherein the alkynyl moiety of $R^3$ are optionally substituted with up to three substituents selected from halogen, —CN, —CHO, acyl, trifluoroalkyl, trialkylsilyl and phenyl, wherein said phenyl is optionally substituted with up to three independently selected $R^{10}$ groups;

wherein the aryl or heteroaryl moiety of $R^3$ is optionally substituted with up to three substituents selected from halogen, —CN, alkyl, alkoxy, perfluoroalkyl or perfluoroalkoxy;

provided that:
at least one of A and A' is not H;
if n is 0, then $R_3$ is not halogen; and
at least one of $R^3$, $R^4$ and $R^5$ is halogen, $C_1$-$C_6$ alkyl, $C_2$-$C_7$ alkenyl, $C_2$-$C_7$ alkynyl, $C_3$-$C_7$ cycloalkyl, —CN, —CHO, acyl, aryl or heteroaryl; or an N-oxide thereof or a pharmaceutically acceptable salt thereof.

39. The product of the process of claim 37.

40. The product of the process of claim 38, where $R^3$ is selected from the group consisting of H, halogen, $CF_3$, $C_1$-$C_6$ perhaloalkyl, $C_1$-$C_6$ alkyl, $C_2$-$C_7$ alkenyl, $C_2$-$C_7$ alkynyl, $C_3$-$C_7$ cycloalkyl, CN, —CHO, acyl, aryl and heteroaryl.

* * * * *